(12) United States Patent
Hsu et al.

(10) Patent No.: US 12,360,039 B2
(45) Date of Patent: Jul. 15, 2025

(54) MULTI-SPECTRAL SCATTERING-MATRIX TOMOGRAPHY

(71) Applicant: University of Southern California, Los Angeles, CA (US)

(72) Inventors: Chia Wei Hsu, Los Angeles, CA (US); Zeyu Wang, Los Angeles, CA (US); Yiwen Zhang, Los Angeles, CA (US)

(73) Assignee: University of Southern California, Los Angeles, IA (US)

( * ) Notice: Subject to any disclaimer, the term of this patent is extended or adjusted under 35 U.S.C. 154(b) by 317 days.

(21) Appl. No.: 17/972,073

(22) Filed: Oct. 24, 2022

(65) Prior Publication Data

US 2023/0128254 A1   Apr. 27, 2023

Related U.S. Application Data

(60) Provisional application No. 63/270,828, filed on Oct. 22, 2021.

(51) Int. Cl.
| | |
|---|---|
| *G01B 9/02091* | (2022.01) |
| *G01N 21/47* | (2006.01) |
| *G03H 1/04* | (2006.01) |

(52) U.S. Cl.
CPC ..... *G01N 21/4795* (2013.01); *G01B 9/02091* (2013.01); *G03H 1/0443* (2013.01); *G03H 2001/0445* (2013.01)

(58) Field of Classification Search
CPC ....... G01N 21/4795; G01N 2021/4711; G01N 2201/105; G01N 21/453; G01N 21/39;

(Continued)

(56) References Cited

U.S. PATENT DOCUMENTS

| | | | | |
|---|---|---|---|---|
| 2005/0270605 A1* | 12/2005 | Moon | ...................... | G03H 1/04 359/3 |
| 2013/0114086 A1* | 5/2013 | Yamada | .................. | H01S 5/141 372/20 |
| 2019/0124247 A1* | 4/2019 | Behrooz | ................ | H04N 23/74 348/77 |

OTHER PUBLICATIONS

Yoon et al., Laser scanning reflection-matrix microscopy for aberration-free imaging through intact mouse skull, (Nov. 12, 2020), Nature Communications, 11, Article No. 5721 With supplementary provided (Year: 2020).*

(Continued)

*Primary Examiner* — Michelle M Iacoletti
*Assistant Examiner* — Judy Dao Tran
(74) *Attorney, Agent, or Firm* — Brooks Kushman P.C.

(57) ABSTRACT

A method for multi-spectral scattering-matrix tomography includes a step of splitting an input light signal into an incident light signal and a reference light signal. The sample light signal is directed to a sample in either a reflection configuration or a transmission configuration such that an output light signal includes light scattered from or transmitted through the sample. The incident signal and the reference light signal are directed to a camera angled to allow for amplitude and phase to be calculated by off-axis holography. A total light signal is measured with a camera that is a coherent sum of the reference light signal and the output signal. The total light signal for each light frequency and each incident angle are collected as collected total light signal data. A computing device derives an image of the sample from a calculated reflection matrix or transmission matrix or both of them.

16 Claims, 26 Drawing Sheets
(17 of 26 Drawing Sheet(s) Filed in Color)

(58) Field of Classification Search
CPC ............. G01B 9/02091; G03H 1/0443; G03H 2001/0445; G03H 2001/266; G03H 1/0866; G03H 1/265; A61B 5/0062; A61B 5/0073; A61B 5/0075
See application file for complete search history.

(56) References Cited

OTHER PUBLICATIONS

Zhang et al., Multi-wavelength multiOangle reflection tomography, (Oct. 1, 2018), Optics Express, vol. 26, No. 20 (Year: 2018).*
Hillman, Efficient holoscopy image reconstruction, (Sep. 4, 2012), Optics Express, vol. 20, No. 19 (Year: 2012).*
Wojtkowski, Ultrahigh-resolution, high-speed, Fourier domain optical coherence tomography and methods for dispersion compensation, (May 31, 2004), Optics Express, vol. 12, No. 11 (Year: 2004).*

* cited by examiner

Optimized spectral intensity
Use a motorized attenuator to minimize the intensity difference at different wavelengths:
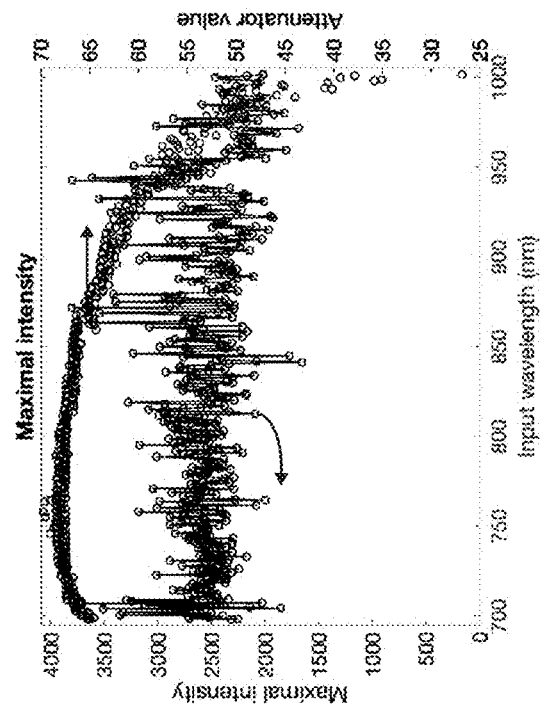
*Fig. 5-2* — After optimization
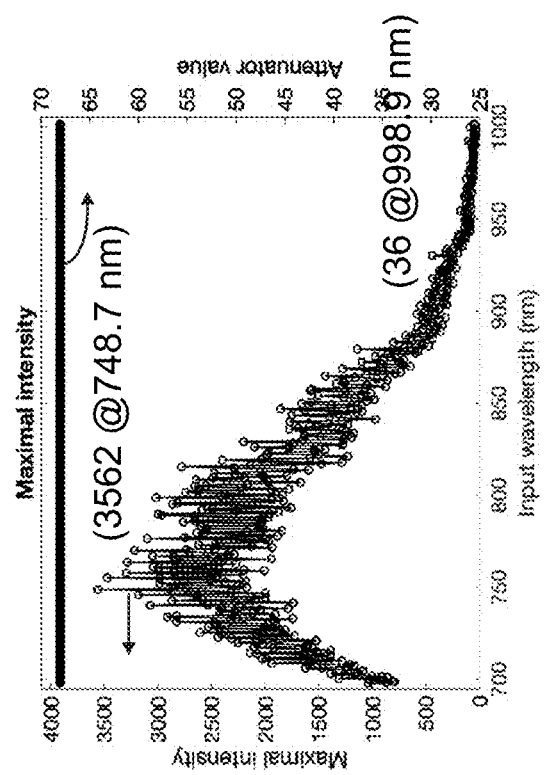
*Fig. 5-1* — Before optimization

Frequency-dependent phase

Relative phase between sample beam and reference beam:

$$\varphi(\omega) = \varphi_0 + \frac{\omega}{c}\left(\sum_i^{\text{sam}} n_i(\omega) L_i - \sum_j^{\text{ref}} n_j(\omega) L_j\right)$$

Target specs:
- 256*256-pixel images, FOV = (50 μm)², at 64,000 frames/second
  (~4 billion pixels/second => ~ 1 billion pixels after phase retrieval)
- Scan 100*100 incident angles
- Repeat for 100 frequencies from 700 nm to 1000 nm
- Total measurement time: $100 \left(\underbrace{0.2 \text{ s}}_{\text{Laser tuning}} + \underbrace{\frac{100*100}{64,000 \text{ s}^{-1}}}_{\text{Camera}}\right) = 36$ sec (92GB data)

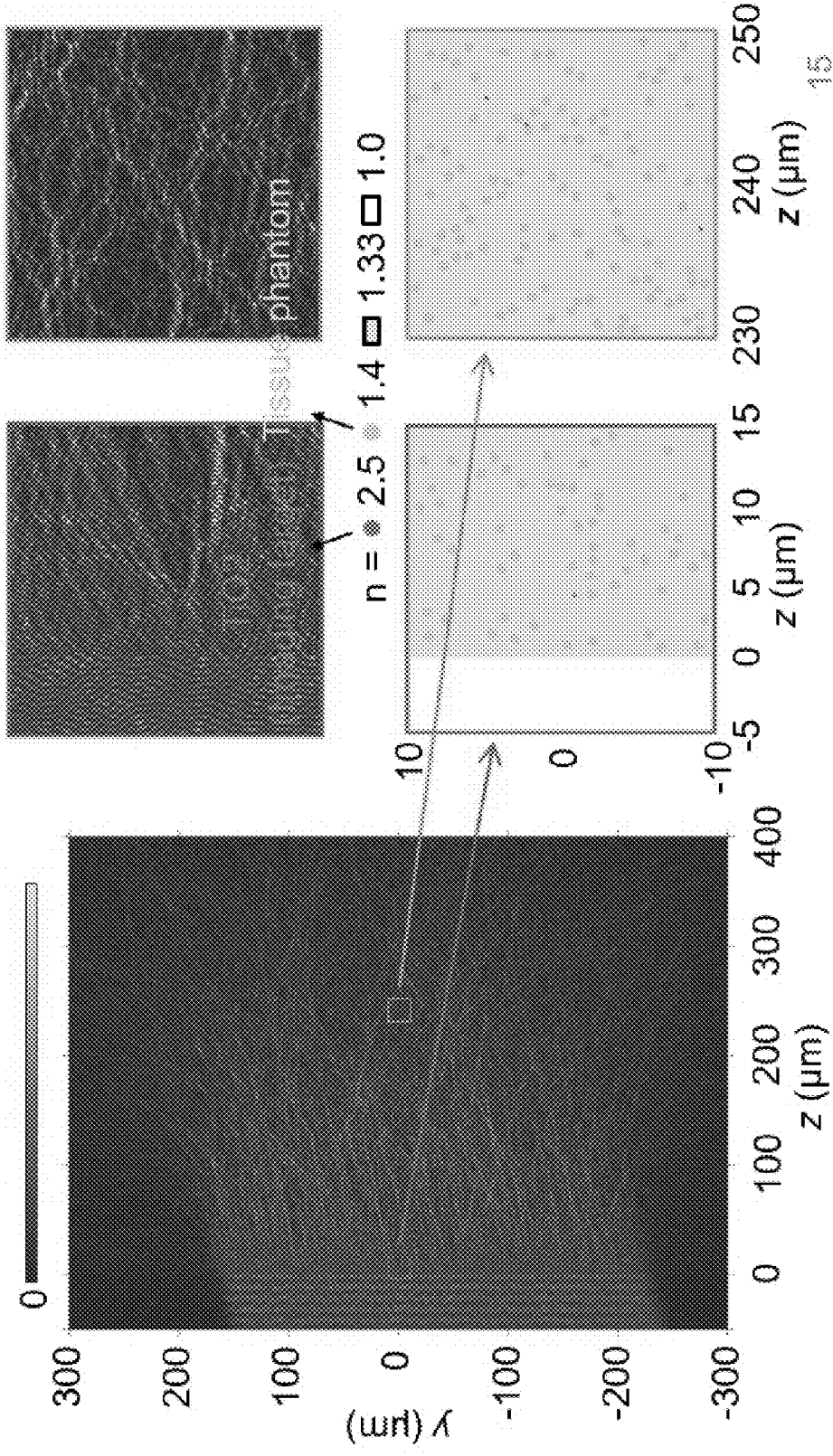

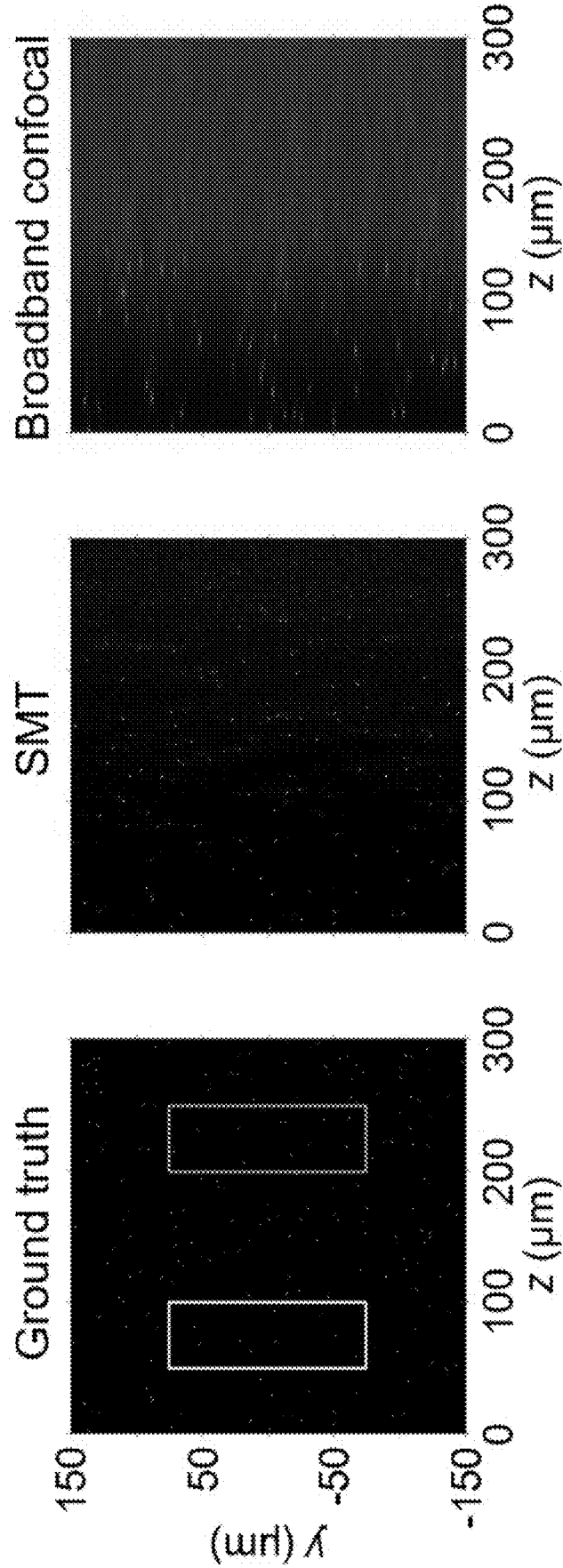
*Fig. 13A*  *Fig. 13B*  *Fig. 13C*

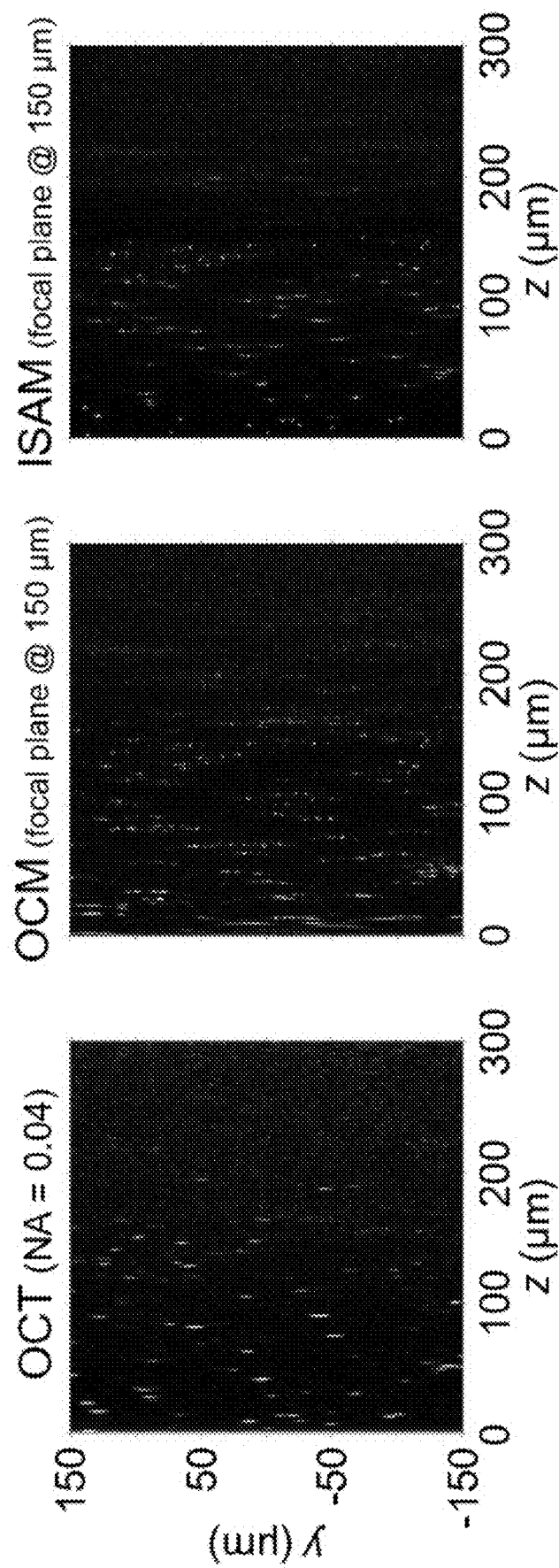

Methods comparison

| | SMT | Confocal | OCT | OCM | ISAM |
|---|---|---|---|---|---|
| Imaging depth | Deepest | Deep | Deep | Deeper | Deeper |
| Lateral resolution | High | High | Low | High near focal plane | High near focal plane & with weak scattering |
| Axial resolution | High | Low | High | High | High |
| Depth scanning | Digital | Mechanical | Digital or mechanical | Mechanical | Digital |
| Index mismatch correction | Digital | Hardware | Not needed | Hardware | Hardware |
| Spatial aberration correction | Digital | Hardware | Hardware or digital | Hardware or digital | Hardware or digital |

Fig. 18

MULTI-SPECTRAL SCATTERING-MATRIX TOMOGRAPHY

CROSS-REFERENCE TO RELATED APPLICATIONS

This application claims the benefit of U.S. provisional application Ser. No. 63/270,828 filed Oct. 22, 2021, the disclosure of which is hereby incorporated in its entirety by reference herein.

TECHNICAL FIELD

In at least one aspect, the present invention relates to imaging techniques with improved depth of field, imaging depth, resolution.

BACKGROUND

Current imaging can only image samples close to a sample's surface. Confocal microscopy is widely used for material characterization and medical imaging. This technique has good lateral resolution but poor axial resolution. Optical coherence tomography is currently used by ophthalmologists to examine a patient's eyes. This technique, while providing good axial resolution, has poor lateral resolution or a high lateral resolution with a limited depth of field (trade-off between lateral resolution and depth of field). The imaging depth and resolution of these methods get degrade when there are sample-induced aberrations.

Accordingly, there is a need for improved imaging techniques with a combined improved axial resolution, lateral resolution, and depth of field.

SUMMARY

In at least one aspect, a method for multi-spectral scattering-matrix tomography is provided. The method includes a step of splitting an input light signal into an incident light signal and a reference light signal. Characteristically, the input light signal is varied over a predetermined frequency range. The incident light signal is directed to a sample in either a reflection configuration or a transmission configuration such that an output light signal includes light scattered from or transmitted through the sample. The incident light signal is varied over a predetermined range of incident angles. The output light signal and the reference light signal are directed to a camera such that the output light signal is directed at a constant angle with respect to the reference light signal to allow for amplitude and phase to be calculated by off-axis holography. A total light signal is measured with a camera that is a coherent sum of the reference light signal and the output light signal. The total light signal for each light frequency and each incident angle as collected total light signal data is collected with a computing device. A computing device is configured to calculate a scattering matrix and/or a reflection matrix and/or transmission matrix from the collected total light signal data and derive an image of the sample from the scattering matrix and/or reflection matrix and/or transmission matrix by summing over angles and summing over light frequencies.

In another aspect, a multi-spectral scattering-matrix tomography system is provided. The system includes a tunable laser that provides an input light signal having a light frequency varied over a predetermined frequency range. A beam splitter is configured to split the input light signal into an incident light signal and a reference light signal. A galvanometer scanner is configured to direct the incident light signal to a sample, wherein the incident light signal is varied over a predetermined range of incident angles. A first set of optical components is configured to direct the incident light signal to the sample in either a reflection configuration or a transmission configuration such that an output light signal includes light scattered from or transmitted through the sample. A second set of optical components is configured to direct the output light signal and the reference light signal. Advantageously, the output light signal is directed to the camera at a constant angle with respect to the reference light signal to allow for amplitude and phase to be calculated by off-axis holography. A camera is configured to measure a total light signal that is a coherent sum of the reference light signal and the output light signal. The system also includes a computing device in electrical communication with the camera, the computing device configured to collect the total light signal for each light frequency and each incident angle as collected total light signal data, to calculate a scattering matrix and/or a reflection matrix and/or transmission matrix from the collected total light signal data; and to derive an image of the sample from the scattering matrix and/or the reflection matrix and/or transmission matrix by summing over angles and summing over light frequencies.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature, objects, and advantages of the present disclosure, reference should be made to the following detailed description, read in conjunction with the following drawings, wherein like reference numerals denote like elements and wherein:

FIGS. 5-1 and 5-2. Plots of the spectral intensity before and after optimization.

FIGS. 12-1, 12-2, 12-3, 12-4, and 12-5. Results of performing full-wave simulations for Maxwell's equations in 2D for a system of $TiO_2$ nanoparticles in a tissue phantom.

FIGS. 13A, 13B, 13C, 13D, 13E, and 13F. Comparison of image reconstruction for various techniques.

FIG. 18. Table comparing SMT and other imaging methods.

DETAILED DESCRIPTION

Figure 1:
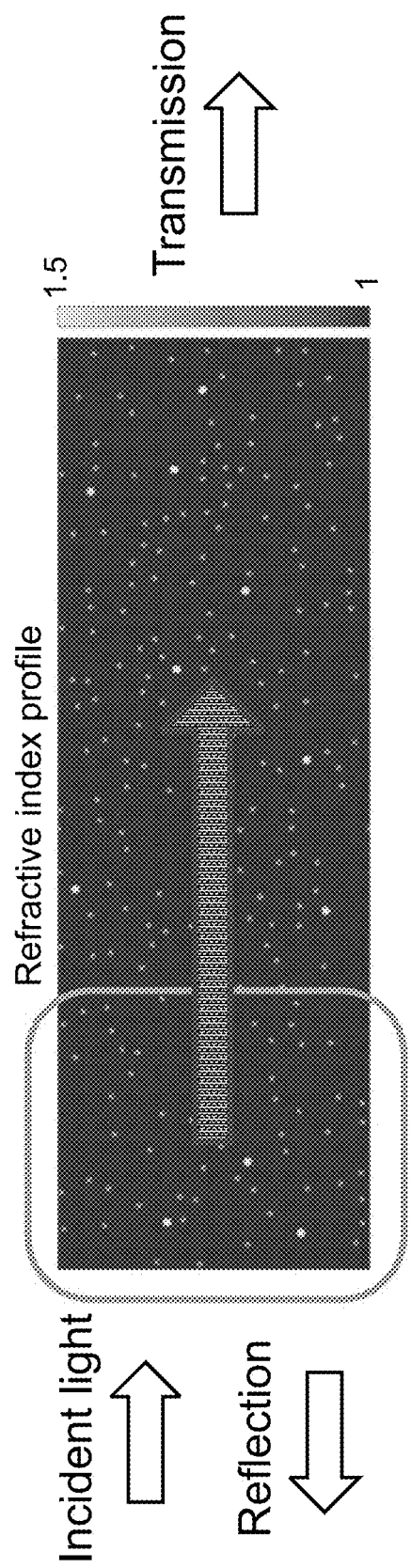
FIG. 1. Schematic illustration of imaging inside a scattering medium.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

When referring to a numerical quantity, in a refinement, the term "less than" includes a lower non-included limit that is 5 percent of the number indicated after "less than." A lower non-includes limit means that the numerical quantity being described is greater than the value indicated as a lower non-included limited. For example, "less than 20" includes a lower non-included limit of 1 in a refinement. Therefore, this refinement of "less than 20" includes a range between 1 and 20. In another refinement, the term "less than" includes a lower non-included limit that is, in increasing order of preference, 20 percent, 10 percent, 5 percent, 1 percent, or 0 percent of the number indicated after "less than."

With respect to electrical devices, the term "connected to" means that the electrical components referred to as connected to are in electrical communication. In a refinement, "connected to" means that the electrical components referred to as connected to are directly wired to each other. In another refinement, "connected to" means that the electrical components communicate wirelessly or by a combination of wired and wirelessly connected components. In another refinement, "connected to" means that one or more additional electrical components are interposed between the electrical components referred to as connected to with an electrical signal from an originating component being processed (e.g., filtered, amplified, modulated, rectified, attenuated, summed, subtracted, etc.) before being received to the component connected thereto.

The term "electrical communication" means that an electrical signal is either directly or indirectly sent from an originating electronic device to a receiving electrical device. Indirect electrical communication can involve processing of the electrical signal, including but not limited to, filtering of the signal, amplification of the signal, rectification of the signal, modulation of the signal, attenuation of the signal, adding of the signal with another signal, subtracting the signal from another signal, subtracting another signal from the signal, and the like. Electrical communication can be accomplished with wired components, wirelessly connected components, or a combination thereof.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10%.

The term "computing device" refers generally to any device that can perform at least one function, including communicating with another computing device. In a refinement, a computing device includes a central processing unit that can execute program steps and memory for storing data and a program code. Examples of computing devices include, but are not limited to, desktop computers, notebook computers, laptop computers, mainframes, mobile phones, headsets such as augmented reality headsets, virtual reality headsets, mixed reality headsets, augmented reality devices, virtual reality devices, mixed reality devices, and the like.

When a computing device is described as performing an action or method step, it is understood that the one or more computing devices are operable to and/or configured to perform the action or method step typically by executing one or more lines of source code. The actions or method steps can be encoded onto non-transitory memory (e.g., hard drives, optical drive, flash drives, and the like).

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

Abbreviations

"CCD" means charged coupled device.
"DOF" means depth of field.
"FWHM" means full-width half-maximum.
"HWP" means half-wave plate.
"ISAM" means interferometric synthetic aperture microscopy.
"NA" means numerical aperture.
"NUFFT" means non-uniform fast Fourier transform.
"OCM" means optical coherence microscopy.
"OCT" means optical coherence tomography.
"PBS" means polarizing beam splitter.
"SMT" means scattering matrix tomography.

Referring to FIG. 1, a schematic illustration of imaging inside a scattering medium is provided. The figure shows a medium with large and small scattering centers dispersed in a medium. In many applications, the medium needs to be probed from the outside in a non-invasive manner. The multi-spectral scattering-matrix tomography systems set forth herein allow for improved imaging of the inside the scattering medium for applications such as biomedical imaging and non-destructive device testing.

Figure 2:
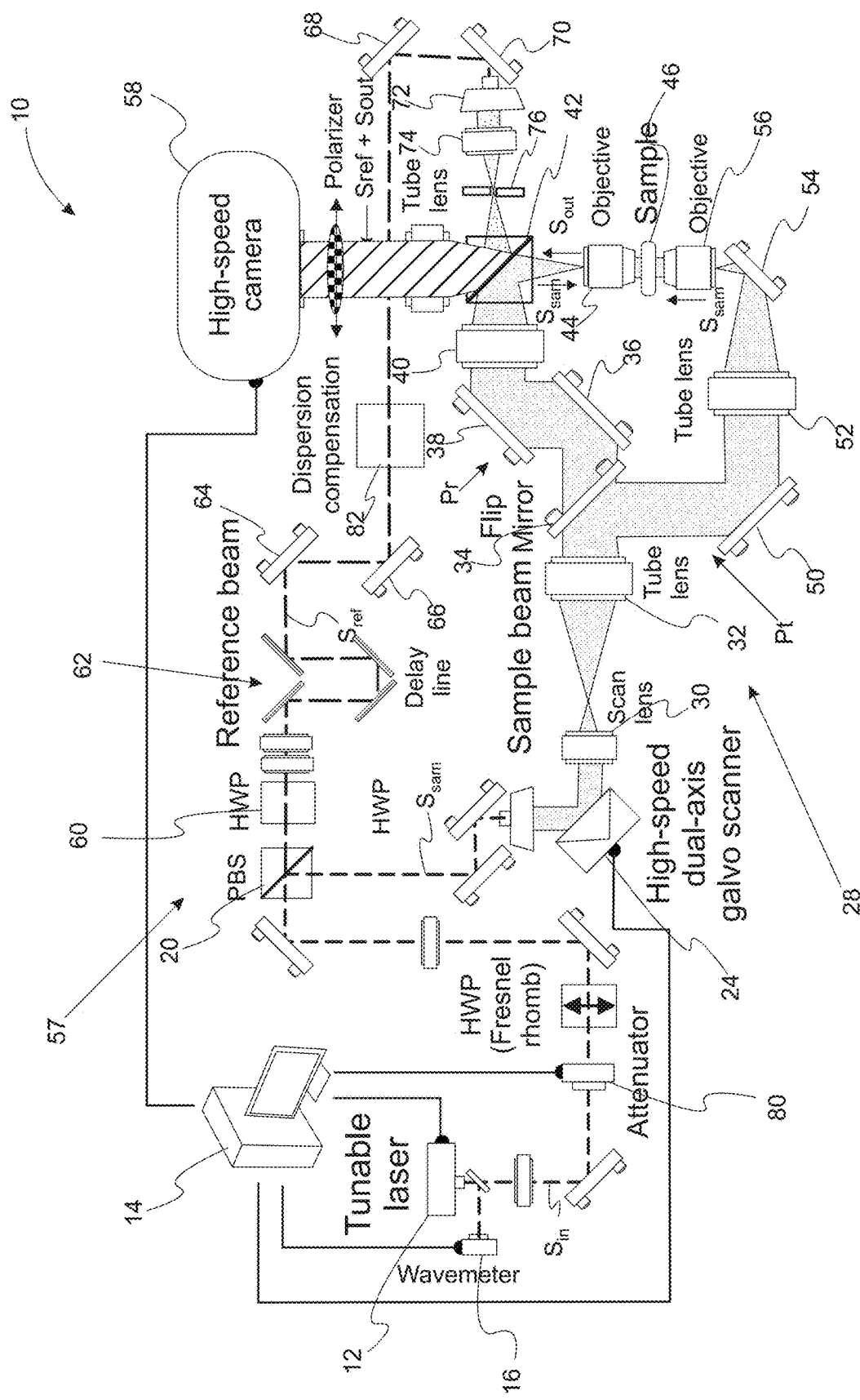
FIG. 2. Schematic of a multi-spectral scattering-matrix tomography system.

Referring to FIG. 2, a schematic of a multi-spectral scattering-matrix tomography system is provided. Multi-spectral scattering-matrix tomography system includes a tunable laser 12 (e.g., a Ti-sapphire laser) that provides an input light signal $S_{in}$ having a light wavelength (and therefore frequency) varied over a predetermined wavelength range (and therefore a predetermined frequency range). In a refinement, the predetermined wavelength range is from 700 nm to 1000 nm (i.e., 430 THz to 300 THz). Tunable laser 12 is in electrical communication with computing device 14. Wavemeter 16 is also in communication with computing device 14 to monitor the frequency of the input light signal. A beam splitter 20 is configured to split the input light signal $S_{in}$ into an incident light signal $S_{sam}$ (sometimes referred to as a sample light signal) and a reference light signal $S_{ref}$. A galvanometer scanner 24 is configured to direct the incident light signal to a sample such that the incident light signal is varied over a predetermined range of incident angles.

A first set of optical components 28 is configured to direct the incident light signal to the sample in either a reflection configuration or a transmission configuration such that an output light signal includes light scattered from or transmitted through the sample. For example, the incident light signal is passed through scan lens 30 and then through tube lens 32. Flip mirror 34 is used to determine if system 10 operates in the reflection configuration or the transmission configuration. When the flip mirror 34 is not in place, path Pr is followed, and the reflection configuration is selected. The incident light signal passes from the flip mirror to mirrors 36 and 38 through lens 40 and then to beam splitter 42. From beam splitter 42, the incident light signal is directed through objective 44 to sample 46. When the flip mirror 34 is in place, path Pt is followed, and the transmission configuration is selected. For example, the incident light signal passes from the flip mirror 34 to mirror 50 and then through tube lens 52. The incident light signal is then directed by mirror 54 through objective 56 and finally to sample 46.

Still referring to FIG. 2, a second set of optical components 57 is configured to direct the output light signal and the reference light signal to high-speed camera 58. The output light signal is directed to the camera at a constant angle with respect to the reference light signal to allow for amplitude and phase to be calculated by off-axis holography. For example, the reference light signal passes through half-wave plate 60 and delay line 62 and then to mirrors 64, 66, 68, and 70. The reference light signal then passes through beam expander 72 and lens 74. The reference light signal passes through spatial filter 76 onto beam splitter 42 where it coherently adds to the output light signal from the sample to form a total light signal. In a refinement, galvanometer scanner 24 and camera 58 are synchronized with a trigger signal.

Still referring to FIG. 2, high-speed camera 58 (e.g., a CCD camera) is configured to measure a total light signal that is a coherent sum of the reference light signal and the output signal. Computing device 14 is in electrical communication with the camera. The computing device is configured to collect the total light signal for each light frequency and each incident angle as collected total light signal data, to calculate a scattering matrix and/or a reflection matrix and/or a transmission matrix from the collected total light signal data, and to derive an image of the sample from the scattering matrix and/or the reflection matrix and/or the transmission matrix by summing over angles and summing over light frequencies.

Still referring to FIG. 2, computing device 14 is configured to calculate the scattering matrix and/or the reflection matrix and/or the transmission matrix is determined by Fourier transforming the collected total light signal data to form a transformed collected total signal data and performing an inverse Fourier transform on a first-order region of the transformed collected total signal data to determine amplitude and phase of the output signal. In this context, the term "scattering matrix" refers to the matrix that is multiplied by a vector formed by the weights of a plurality of incident plane waves that when superimposed form the incident light signal (i.e., the input) to provide a vector formed by the weights of a plurality of scattered plane waves that when superimposed form the scattered light signal (i.e., the output) where the scattered light signal is the light scattered from a sample. When only the scattered light from the opposite side of the sample is considered, the scattering matrix is referred to as the transmission matrix. When only the scattered light from the same side of the sample is considered, the scattering matrix is referred to as the reflection matrix. The scattering matrix can be measured noninvasively as shown below. Once the scattering matrix or reflection matrix is determined, the response of a system can be synthesized given an arbitrary input light signal. Advantageously, this allows the ability to digitally achieve perfect spatio-temporal focusing with both input spatial gating, output spatial gating, and time gating. With respect to the incident light signal, a superposition of plane waves across different incident angles can be used to focus the incident light signal at a predetermined position $r_0$ to provide input spatial gating as shown by the following equation:

$$\sum_{k_{in}} e^{ik_{in} \cdot (r-r_0) - i\omega t}$$

Similarly, time gating is obtained when the summation is over frequencies. For time gating, a pulse is obtained that arrives at position $r_0$ at time t equal to 0 as shown in the following equation:

$$\sum_{\omega} e^{ik_{in} \cdot (r-r_0) - i\omega t}$$

Therefore, if summations are performed over both $k_{in}$ and $\omega$, a spatio-temporal focusing input is obtained as follows:

$$\sum_{\omega} \sum_{k_{in}} e^{ik_{in} \cdot (r-r_0) - i\omega t}$$

Alternatively, this can be expressed as an integral over frequencies w as follows:

$$\int d\omega \sum_{\omega} e^{ik_{in} \cdot (r-r_0) - i\omega t}$$

This results in the incident light signal being focused at $r_0$ at time t equal to 0.

In a variation, the hyper-spectral reflection matrix is measured. The reflection matrix can provide the complex amplitude of reflection to different outgoing angles given different incident angle directions across different frequencies. Once this data is obtained, the incident plane wave can be digitally synthesized to be focused at a predetermined position $r_0$ as shown above by multiplying by the reflection matrix to give the reflective light to different outgoing directions. One can then sum over the different outgoing waves and evaluate the outgoing wave at the same position $r_0$. This is where the response is maximized if we have scattering going on at this position. This procedure gives the output spatial gating. To do a time gating, a summation over frequency is performed as described above to provide the response at time t=0. Overall, this triple summation gives us a response that will be maximized when there is a target at position $r_0$. Therefore, squaring the response gives us a real intensity that can be scanned across the positions $r_0$ giving 3D volumetric image. This combination of spatial gating and time gating can be performed simultaneously across the entire volume. Advantageously, there is no longer any tradeoff between depth of focus and lateral resolution. This triple summation is described by the following formula:

$$I_{SMT}(r_0) = \left| \sum_{\omega} \sum_{k_{out}} \sum_{k_{in}} e^{i(k_{out} - k_{in}) \cdot r_0} S(\omega, k_{out}, k_{in}) \right|^2$$

where:
$I_{SMT}$ is the image intensity as a function of position $r_0$ in the sample;
$r_0$ is a position vector of a point in the sample;
$S(\omega, k_{out}, k_{in})$ is the element of the scattering matrix for the incidence channel with $k_{in}$ and the reflection channel with $k_{out}$;
$k_{in}$ is the wavevector of the incident light signal;
$k_{out}$ is the wavevector of the output (i.e., reflected) light signal; and
$\omega$ is the light frequency. Alternatively, the image intensity is found from the following formula when system 10 is in the reflection configuration where the integral over $\omega$ is approximated by a summation over $\omega$:

$$I_{SMT}(r_0) = \left| \sum_{\omega} \sum_{k_{out}} \sum_{k_{in}} e^{i(k_{out} - k_{in}) \cdot r_0} R(\omega, k_{out}, k_{in}) \right|^2$$

where:
$I_{SMT}$ is the image intensity as a function of position $r_0$ in the sample;
$r_0$ is a position vector of a point in the sample;
$R(\omega, k_{out}, k_{in})$ is the element of the reflection matrix for the incidence channel with $k_{in}$ and the reflection channel with $k_{out}$;
$k_{in}$ is the wavevector of the incident light signal;
$k_{out}$ is the wavevector of the output (i.e., reflected) light signal; and
$\omega$ is the light frequency.
In a variation, the image intensity is found from the following formula when system 10 is in the transmission configuration where the integral over $\omega$ is approximated by a summation over $\omega$:

$$I_{SMT}(r_0) = \left| \sum_{\omega} \sum_{k_{out}} \sum_{k_{in}} e^{i(k_{out} - k_{in}) \cdot r_0} T(\omega, k_{out}, k_{in}) \right|^2$$

where:
$I_{SMT}$ is the image intensity as a function of position $r_0$ in the sample;
$r_0$ is a position vector of a point in the sample;

T(ω, $k_{out}$, $k_{in}$) is the element of the transmission matrix for the incidence channel with $k_{in}$ and the reflection channel with $k_{out}$;

$k_{in}$ is the wavevector of the incident light signal;

$k_{out}$ is the wavevector of the output (i.e., reflected) light signal; and

ω is the light frequency.

In a refinement, computing device 14 is configured to determine an image intensity from the following equation when system 10 is in the reflection configuration:

$$I(r) \propto \left| \int d\omega \sum_{b,a} e^{ik_b \cdot r} r_{ba} e^{-ik_a \cdot r} \right|^2$$

where:

I(r) is the image intensity as a function of position r in the sample;

r is a position vector of a point in the sample;

$r_{ba}$ is the element of the reflection matrix for the a-th incidence and b-th reflection channel;

a is a label for an angle of incidence;

b is a label for an angle of reflection;

$k_a$ is the wavevector of the incident light signal;

$k_b$ is the wavevector of the output (i.e., reflected) light signal; and

ω is the light frequency. It should be noted that the image intensity is expressible as:

$I(r) \propto |\int d\omega (A_r^{Born}) \dagger R|^2$, where R is the reflection matrix and $A_r^{Born}$ is the Born matrix. Therefore, I(r) is calculated in the context of the Born Approximation where the multiple scattering events are ignored. However, the summing over frequencies and angle of incidence allows for multiple-scattering contributions add in quasi-random phase, thereby canceling. Attached Exhibit A provides a derivation of $A_r^{Born}$. Exhibit A is part of the specification and incorporated herein in its entirety.

In another refinement, image intensity is determined from the following equation when system 10 is in the transmission configuration:

$$I(r) \propto \left| \int d\omega \sum_{b,a} e^{ik_b \cdot r} t_{ba} e^{-ik_a \cdot r} \right|^2$$

where:

I(r) is the image intensity as a function of position r in the sample;

r is a position vector of a point in the sample;

$t_{ba}$ is the element of the transmission matrix for the a-th incidence and b-th transmitted channel;

a is a label for an angle of incidence;

b is a label for an angle of transmitted light;

$k_a$ is the wavevector of the incident light signal;

$k_b$ is the wavevector of the output light signal; and

ω is the light frequency.

In summary, the components of SMT summation over incident angles provide input spatial gating, summation over output angle gives us output spatial gating, and summation over frequency gives time gating. It should be appreciated that the measured reflection matrix is not focused either in time or in space. However, all of this refocusing is performed digitally during post-processing. When the triple summation is performed to give an image, the single scattering signals from the targets add up in phase. Meanwhile, the multiple scattered light signal do not add up in phase in the summations and, therefore, are attenuated (e.g., rejected). In addition to this threefold gating, SMT also allows correction for various aberrations digitally. For example, there is typically an index change going from air to the sample target which degrades the focusing quality. This can be corrected for by choosing momentum $k_{in}$ and $k_{out}$ by using the momentum inside the sample. In another example, there are often aberrations and dispersion from the optical system. These can be corrected for by measuring the reflection matrix of a mirror which would be one if there is no system aberration. Therefore, minus the phase of the mirror reflection matrix provides correction for both the chromatic and spatial aberrations of the optical elements. In another example, there can also be dispersion from the sample which can be reduced by optimizing spectral phase in the frequency summation. Finally, there can also be spatial aberrations introduced by the sample target. Similarly, these latter aberrations can be corrected for by optimizing the "in-coming"-angle- and the "outgoing"-angle-dependent phases during the angular summations. Therefore, scattering matrix tomography provides not only spatio-temporal gating across whole volume but a comprehensive correction for various aberrations that can be done digitally.

Figure 3A:
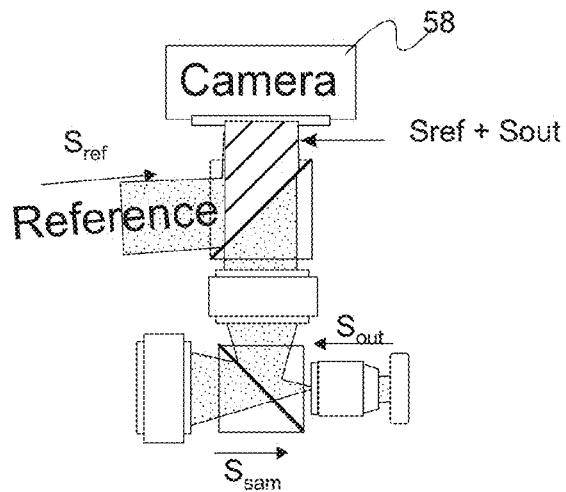
FIG. 3A. Schematic illustrating the off-axis holography method.
Figure 3B:
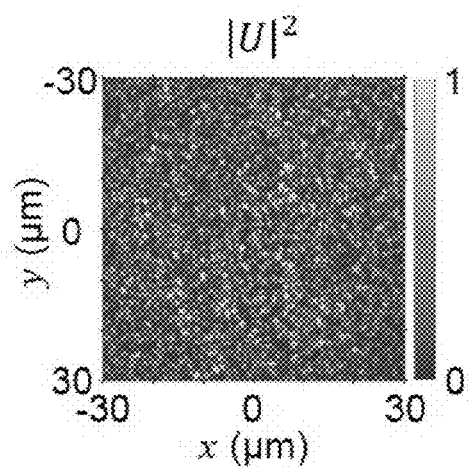
FIG. 3B. Map of the output light signal $S_{out}$'s intensity without being combined with the reference light signal $S_{ref}$.
Figure 3C:
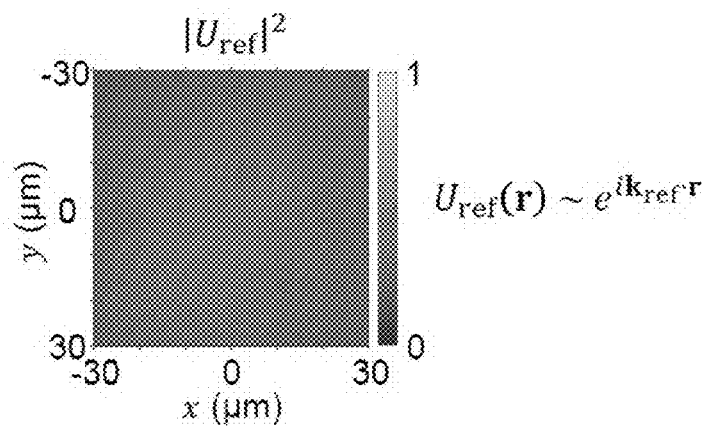
FIG. 3C. Map of the reference light signal $S_{out}$'s intensity without being combined with output light signal $S_{out}$.
Figure 3D:
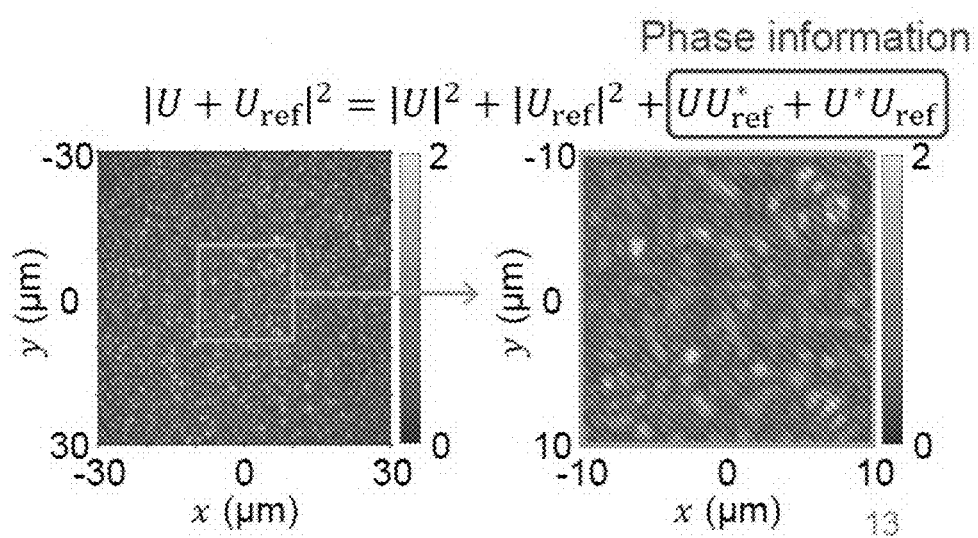
FIG. 3D. Map of the combined total signal from which amplitude and phase can be extracted.

FIGS. 3A-D and 4 depict the operation of the off-axis holograph technique that is implemented by a multi-spectral scattering-matrix tomography system 10. FIG. 3A schematically depicts an off-axis holograph technique in which the output light signal $S_{out}$ is directed to camera 58 at a constant angle with respect to the reference light signal $S_{ref}$ to allow for amplitude and phase to be calculated by off-axis holography. FIG. 3B depicts a map of the output light signal $S_{out}$'s intensity without being combined with the reference light signal $S_{ref}$ while FIG. 3C depicts a map of the reference light signal $S_{ref}$'s intensity without being combined with output light signal $S_{out}$. FIG. 3D provides a map of the combined total signal intensity from which amplitude and phase can be extracted.

Figure 4:
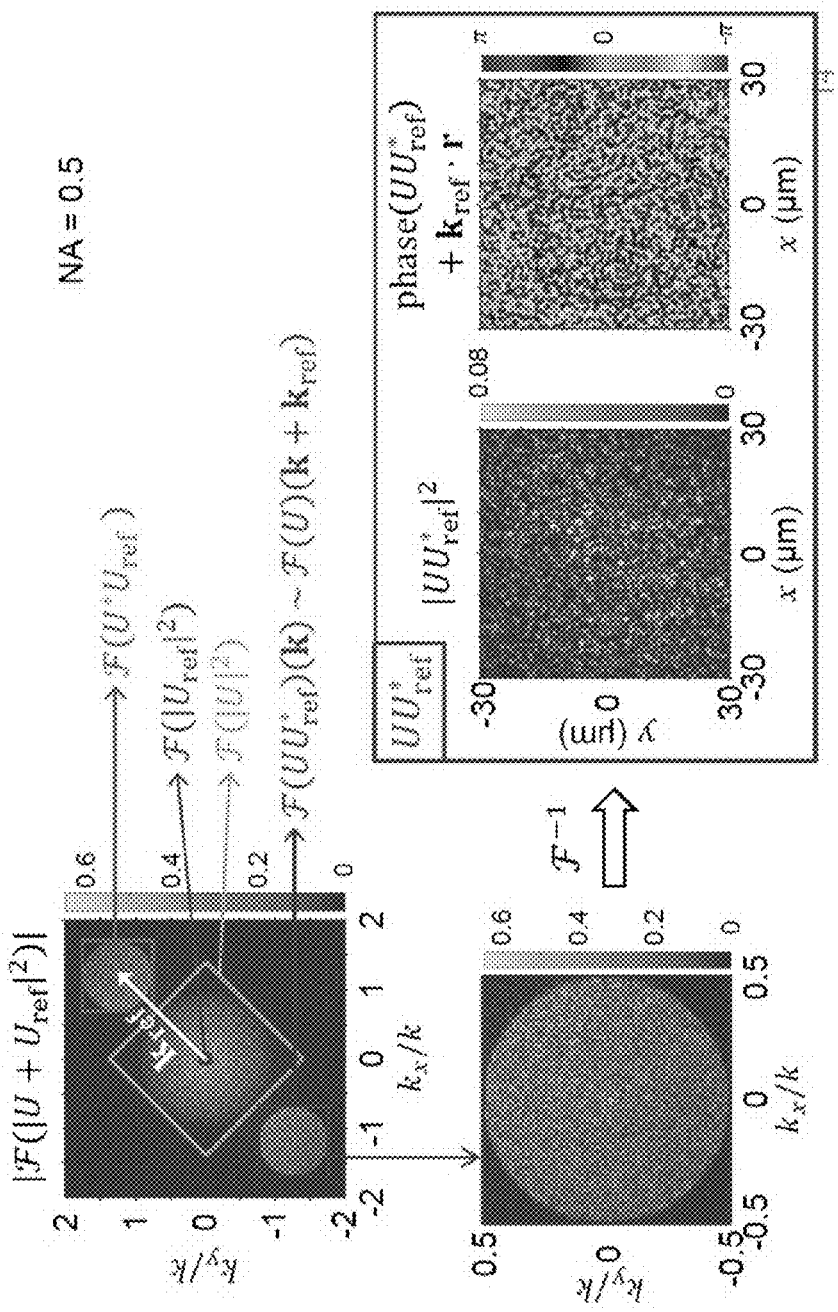
FIG. 4. Maps illustrating the off-axis holography technique.

FIG. 4 provides plots illustrating the extraction of amplitude and phase information from the combined total light signal ($S_{out}+S_{ref}$). In this method, the collected total light signal data for a single incident angle is Fourier transformed to form a transformed collected total signal data. An inverse Fourier transform is then performed on a first-order (e.g., −1 or 1 order) region (i.e., by cropping the Fourier space) of the transformed collected total signal data to determine the amplitude and phase of the output signal. This method allows row of values of the reflection matrix (or transmission matrix) to be calculated. The entries for each row is the $k_b$ vector (e.g. kx and ky for each output channel b) for the output channel b. This reflection matrix (or transmission matrix) is constructed by scanning angles of incidence.

Referring to FIGS. 2 and 5, the effects of the variation of input light signal intensity of the varying frequencies are illustrated. FIG. 5 provides plots of the spectral intensity before and after optimization. As set forth above, the input light signal $S_{in}$ is modified over the predetermined frequency range. Therefore, system 10 can include light attenuator 80 configured to modify input light signal intensity over the predetermined frequency range to minimize light intensity differences.

Figure 6:
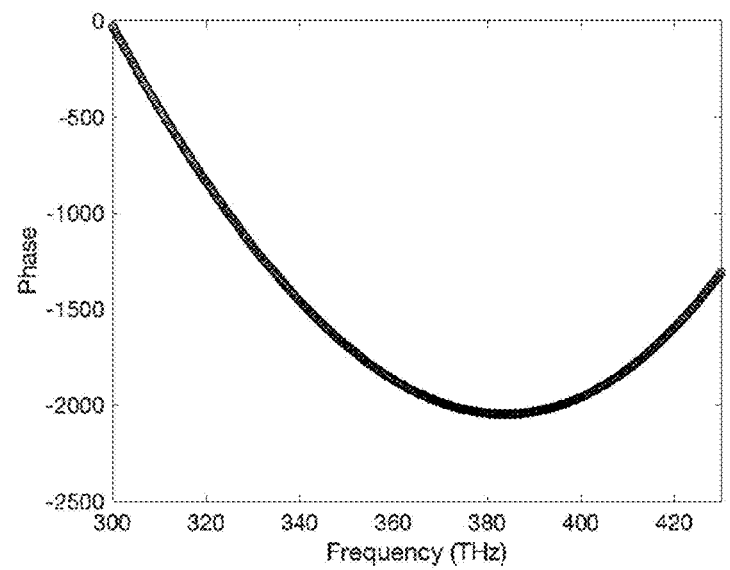
FIG. 6. Plot showing a frequency-dependent phase.

Referring to FIGS. 2 and 6, the effects of the frequency-dependent phase are illustrated. To mitigate the effect of the frequency-dependent phase, system 10 can include dispersion compensator 82 is the reference light signal path.

Figure 7:
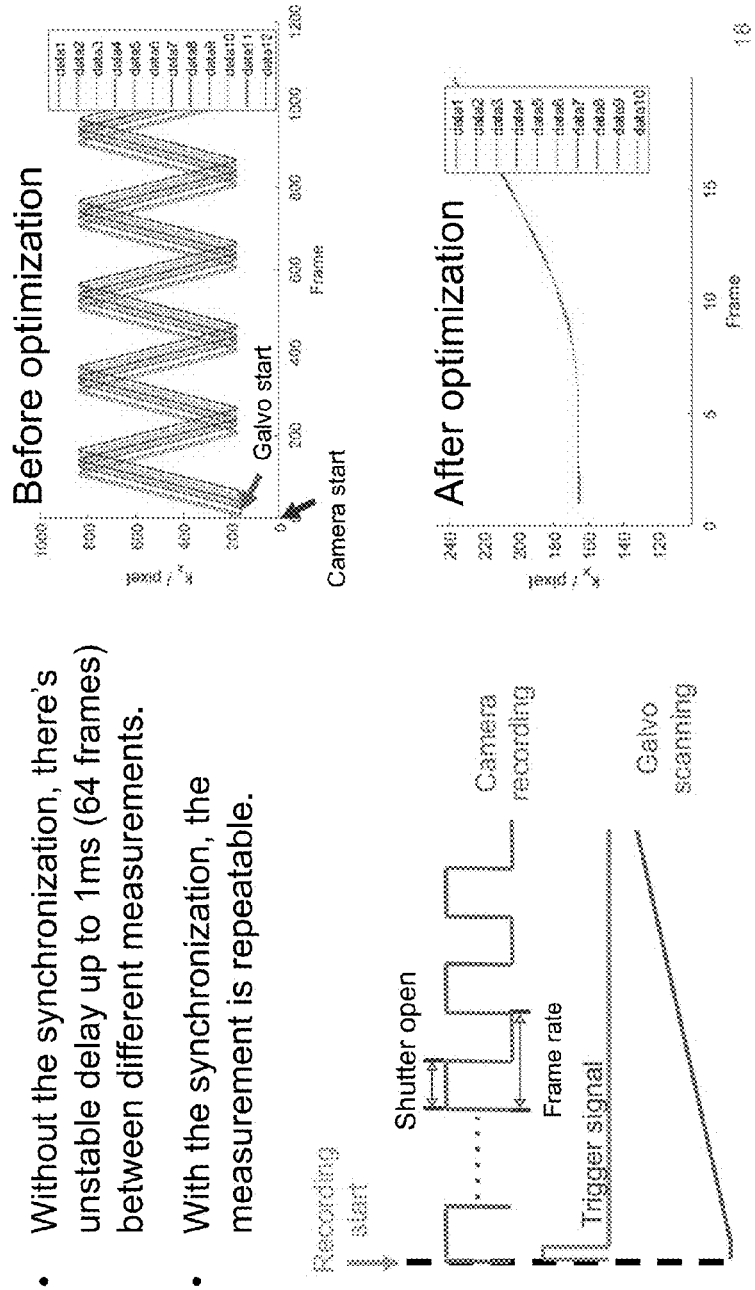
FIG. 7. Plots showing that without the synchronization, there is an unstable measurement delay.

Referring to FIGS. 2 and 7, the effect for synchronizing the galvanometer scanner and the camera are illustrated. As set forth above, galvanometer scanner 24 and the camera 58 are synchronized with a trigger signal from one of the devices to the other. FIG. 7 shows that without the synchronization, there is an unstable delay of up to 1 ms between different measurements. With synchronization, the measurements are repeatable.

Figure 8:
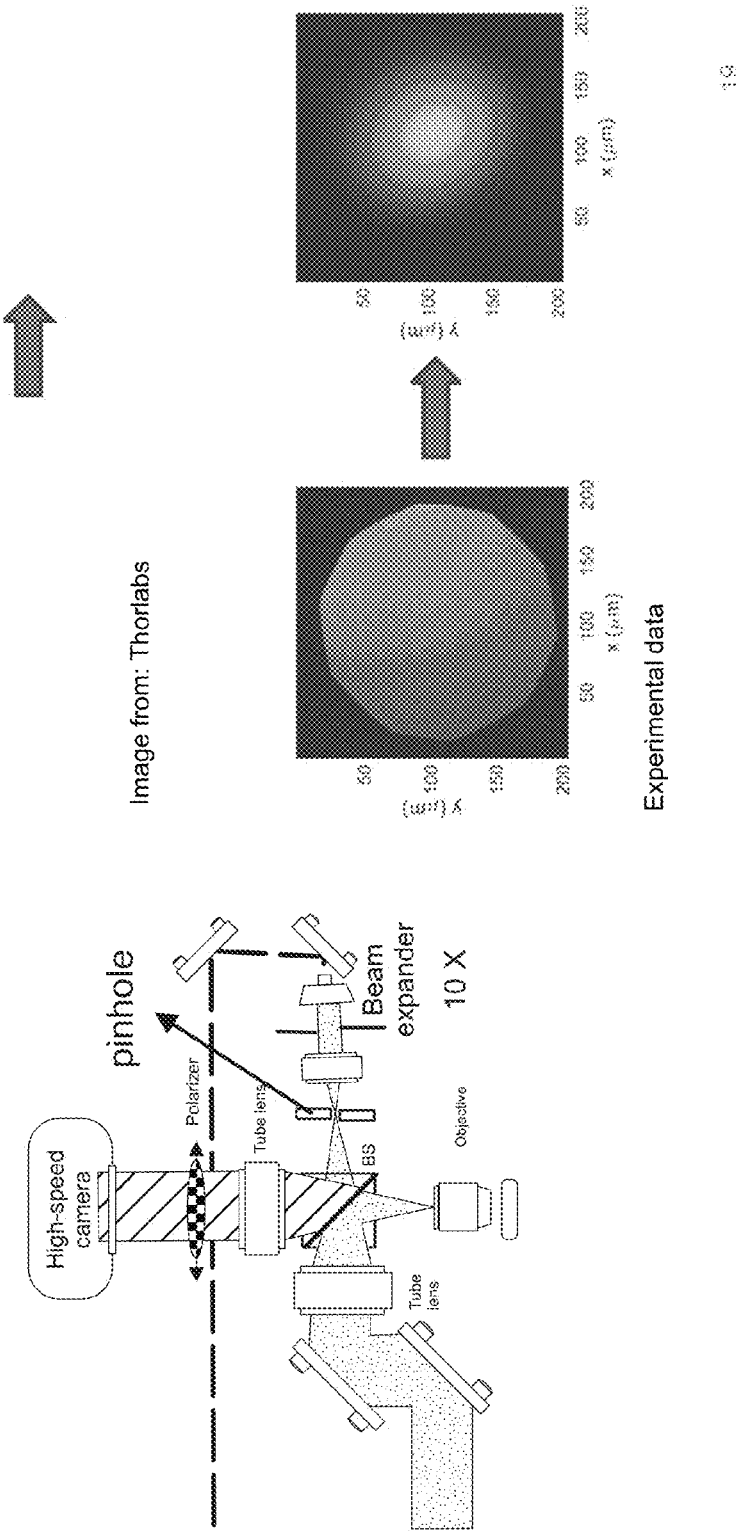
FIG. 8. Schematic and maps illustrating that the reference light signal can be spatially filtered to provide a cleaner and Gaussian-like beam profile.

Referring to FIGS. 2 and 8, the effects of filtering the reference light signal are provided. As set forth above, system 10 includes spatial filter 76 configured to spatially filter the reference light signal to provide a cleaner and Gaussian-like beam profile. FIG. 8 confirms that the reference light signal can be spatially filtered to provide a cleaner and Gaussian-like beam profile.

Figure 9:
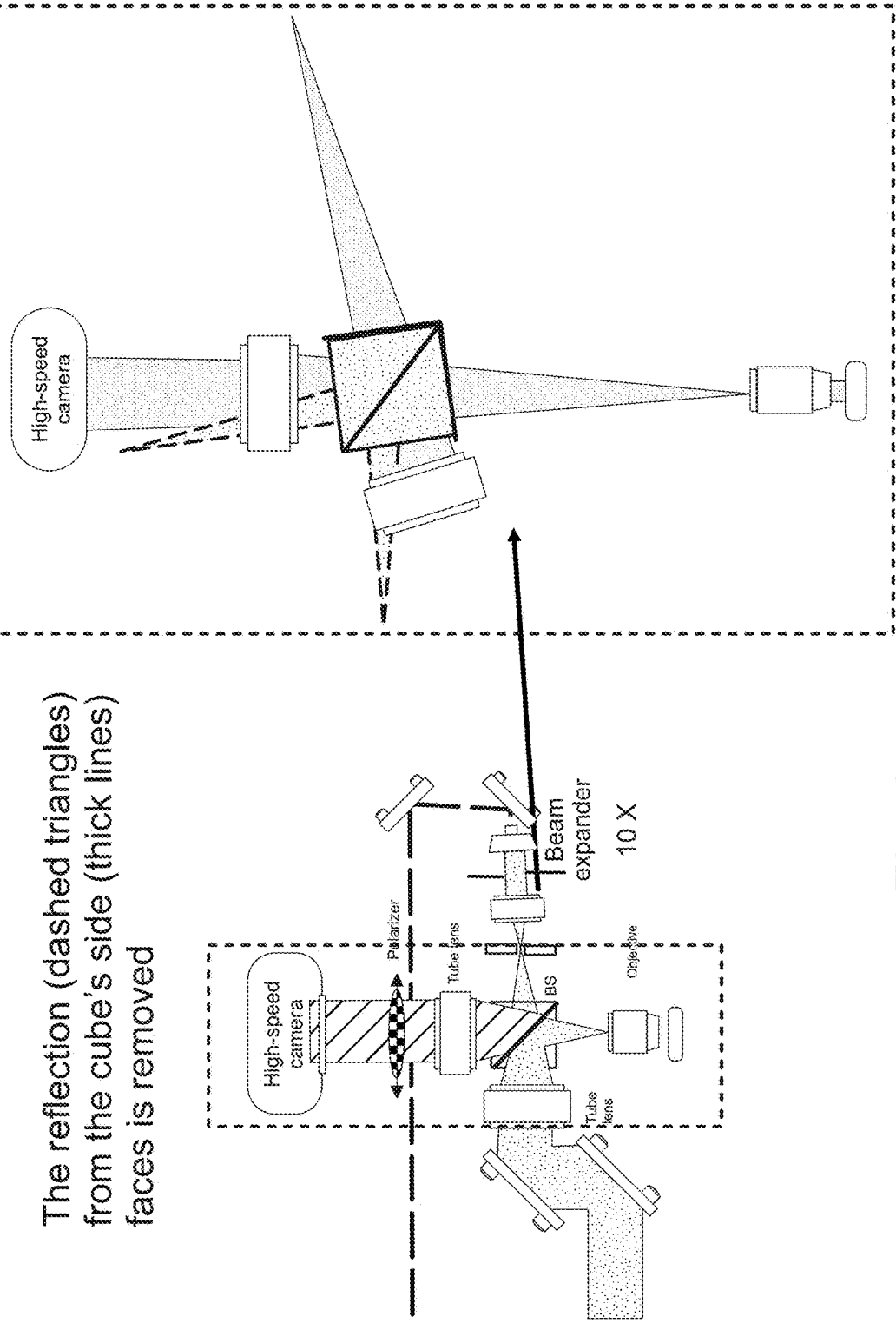
FIG. 9. Schematic illustrating the advantages of a misaligned beam splitter.

Referring to FIGS. 2 and 9, the advantages of a non-45 degree beam splitter are provided. The non-45 degree alignment of beam splitter 42 allows for spurious light signals from the beam split to avoid camera 58.

Figure 10:
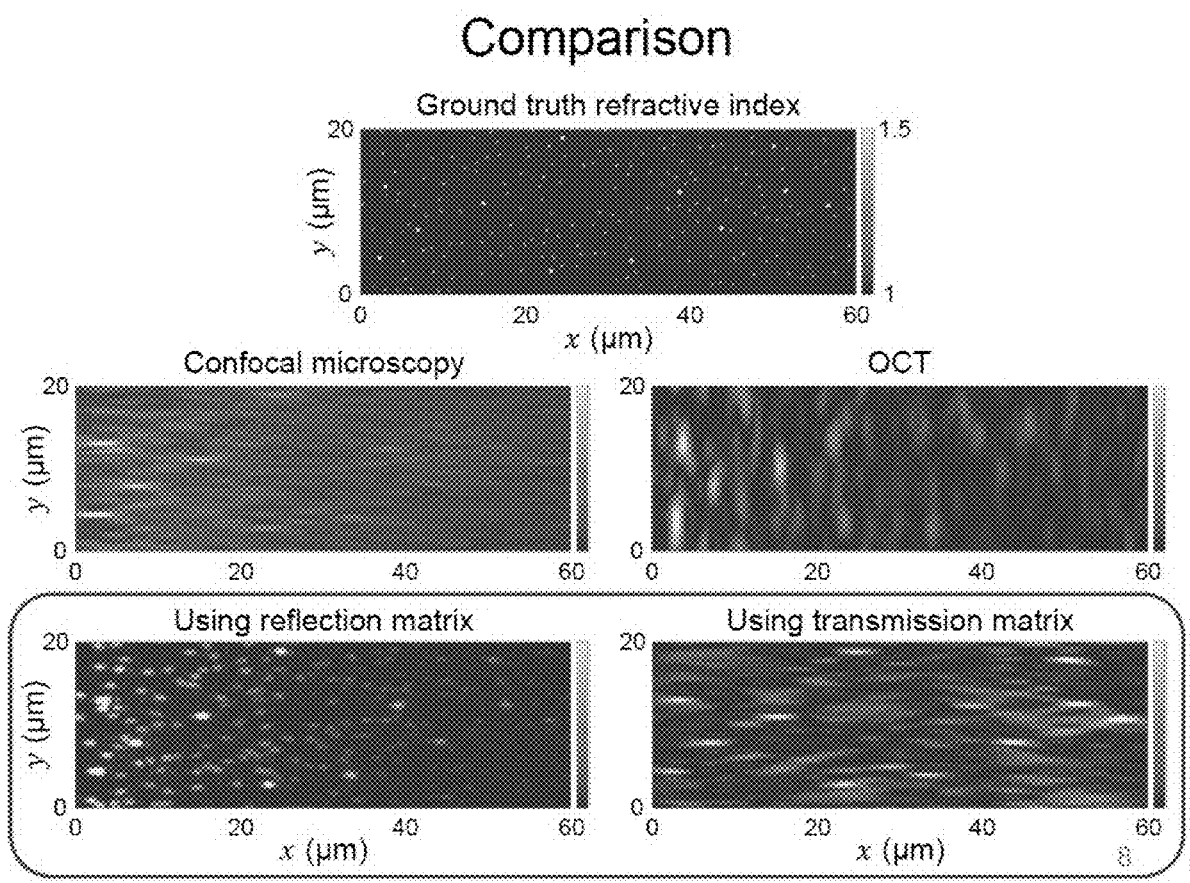
FIG. 10. Maps comparing confocal microscopy, OCT, and the methods set forth above are provided.

Referring to FIG. 10, maps comparing conformal microscopy, OCT, and the methods set forth above are provided. The multi-spectral scattering-matrix tomography method set forth herein provides improved lateral resolution ($0.4\lambda/NA$) and improved axial resolution ($0.44\lambda^2/\Delta\lambda$)

Figure 11:
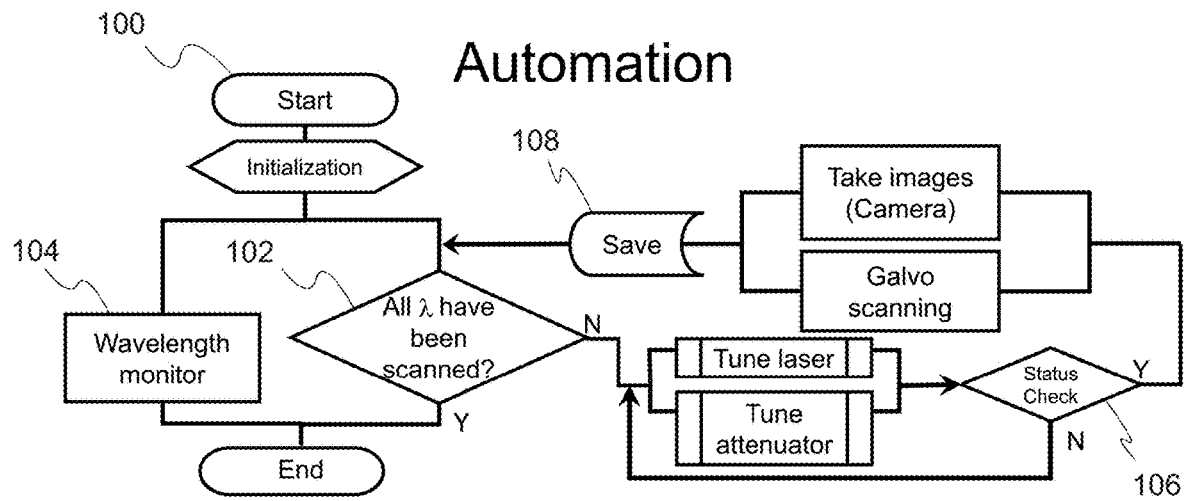
FIG. 11. Flowchart depicting automation of the method set forth above is provided.

Referring to FIG. 11, a flowchart depicting automation of the method set forth above are provided. In step 100, the SMT system is initialized. In decision box 102, a determination is made if all the desired wavelengths of light have been scanned. If the entire predetermined wavelength range has been scanned, the method stops. If the entire predetermined wavelength range has not been scanned the laser light source and attenuator are tuned to a given wavelength.

FIG. 12 provides the results of performing full-wave simulations for Maxwell's equations in 2D for a system of $TiO_2$ nanoparticles in a tissue phantom. The intensity profile on the left is for incident light contacting imaging target with an angle of incidence of about 15°. FIG. 12-2 and FIG. 12-3 show the ground truth in the pink window near the front of the sample and the green window deeper into the sample. The red dots are TiO2 particles that we want to image, which are buried in the tissue phantom consisting of many larger lower index particles. FIG. 12-4 and FIG. 12-5 provide the intensity profiles in these two windows. It is observed that near the sample front there is visible correspondence between the scatter location and the high intensity profile, but deeper into the sample there is no longer such visible. In the full-wave simulation, we get the reflected waves and project them into different reflected angles to mimic experimentally measurement and that gives us one column of the reflection matrix. Conventionally, one would have to perform these simulations repeatedly across hundreds of incident angles to build the reflection matrix. However, we have developed an efficient software called MESTI (Maxwell's Equations Solver with Thousands of Inputs) which is open source of Gitbhub which can compute the whole scattering matrix simultaneously efficiently (https://github.com/complexphoton/mesti.m). Using this software, one can predict reflection matrix $R(\omega, k_{out}, k_{in})$ of this 400 micron by 600 micron system across 450 wavelengths (700 to 1000 nm) at 0.5 numerical aperture (about 600~900 angles per wavelength).

FIGS. 13A, 13B, 13C, 13D, 13E, and 13F provide a comparison of image reconstruction for various techniques. FIG. 13A provides the ground truth showing the location of $TiO_2$ nanoparticles and FIG. 13A we get by evaluating this equation for scattering matrix tomography. These figures show that locations of the $TiO_2$ nanoparticles can be faithfully reconstructed with high resolution even though only data in the reflection in the far field is used. In SMT, a coherent summation of the frequencies is performed. As a comparison in FIG. 13C, an incoherent summation of frequencies is performed by summing over the intensities. This mimics confocal microscopy with the confocal spatial gating in the input and output. However, there is no temporal gating. It is observed that axial resolution is reduced because of the lack of time gating.

Figure 14:
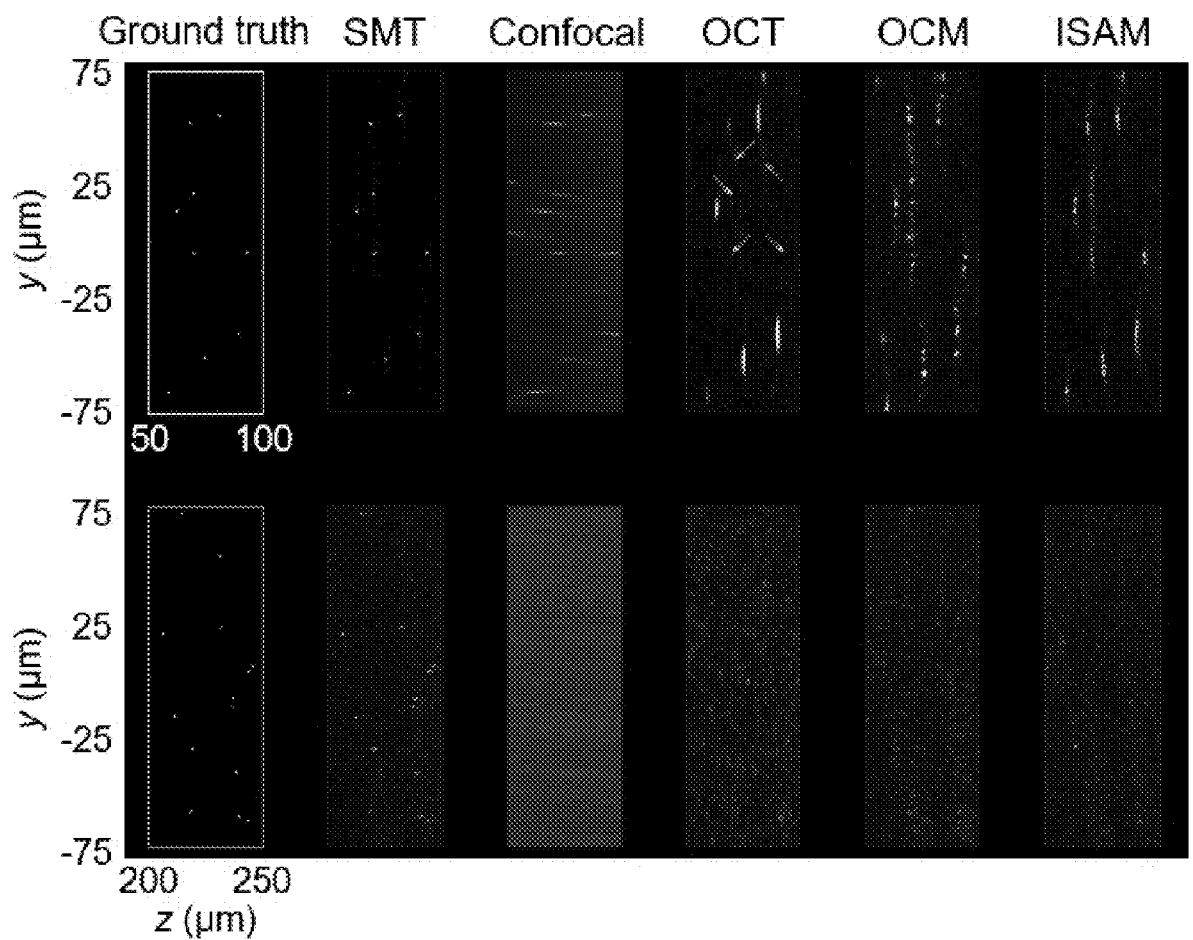
FIG. 14. Zoomed in imaging reconstruction for the reconstructions of FIG. 13.

FIGS. 13D, 13E, and 13F provide simulations that mimic what happens in the OCT, OCM, and ISAM. In the OCT experiment, the numerical aperture is low such that the depth of field is large. Here the lateral resolution is reduced and also imaging depth is reduced. At the focal plane OCM can have high resolution but the resolution degrades away from the focal plane and again, doesn't image as deep. ISAM can improve the lateral resolution near the surface of the sample because scattering is weak there. However, ISAM's performance is still limited at other locations in the sample target. This is because in ISAM the output always depends on the input so that its gating efficiency decreases away from the focal plane. FIG. 14 provides zoomed in imaging reconstruction for the reconstructions of FIG. 13. At the front part of the sample, SMT gives a high resolution image. In contrast, broadband confocal has a lower axial resolution and OCT has a low lateral resolution. It is observed that several targets missed by OCT while features of OCT that do not correspond to a real target are observed in the images. OCM and ISAM do not work very well at the front part of the sample because they are far away from their focal plane. Deeper inside the target sample, SMT can still reconstruct images with high resolution and deeper depths in contrast to the other imaging methods.

Figure 15:
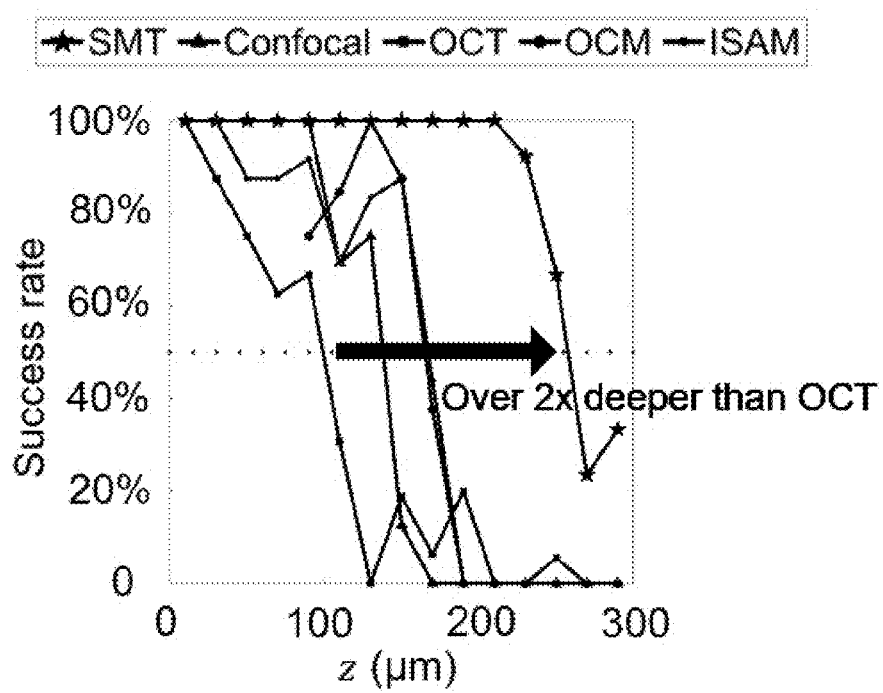
FIG. 15. Success rates for particle identifications in constructed images.

FIG. 15 provides success rates for particle identifications in reconstructed images. Since the ground nanoparticle locations for the simulations are known, the success rate of the images in identifying the particle locations can be determined. If the imaging depth is defined as where the success rate maintains above 50%, it is observed that SMT achieves a depth of more than 2× deeper than OCT.

Figure 16:
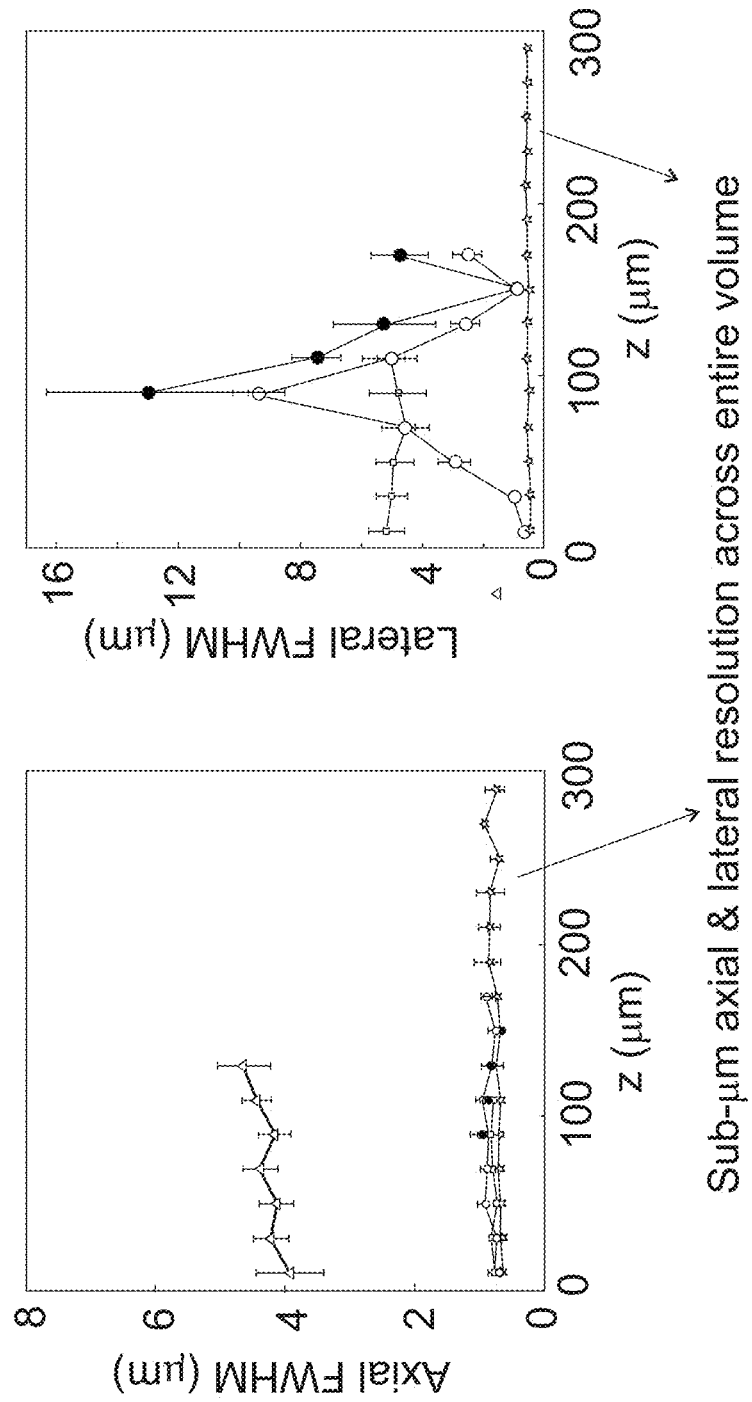
FIG. 16. Axial and lateral resolution comparisons for various imaging techniques.

FIG. 16 provides axial and lateral resolution comparisons for various imaging techniques. SMT is observed to provide very good sub-micron axial and lateral resolution across the entire volume.

Figure 17:
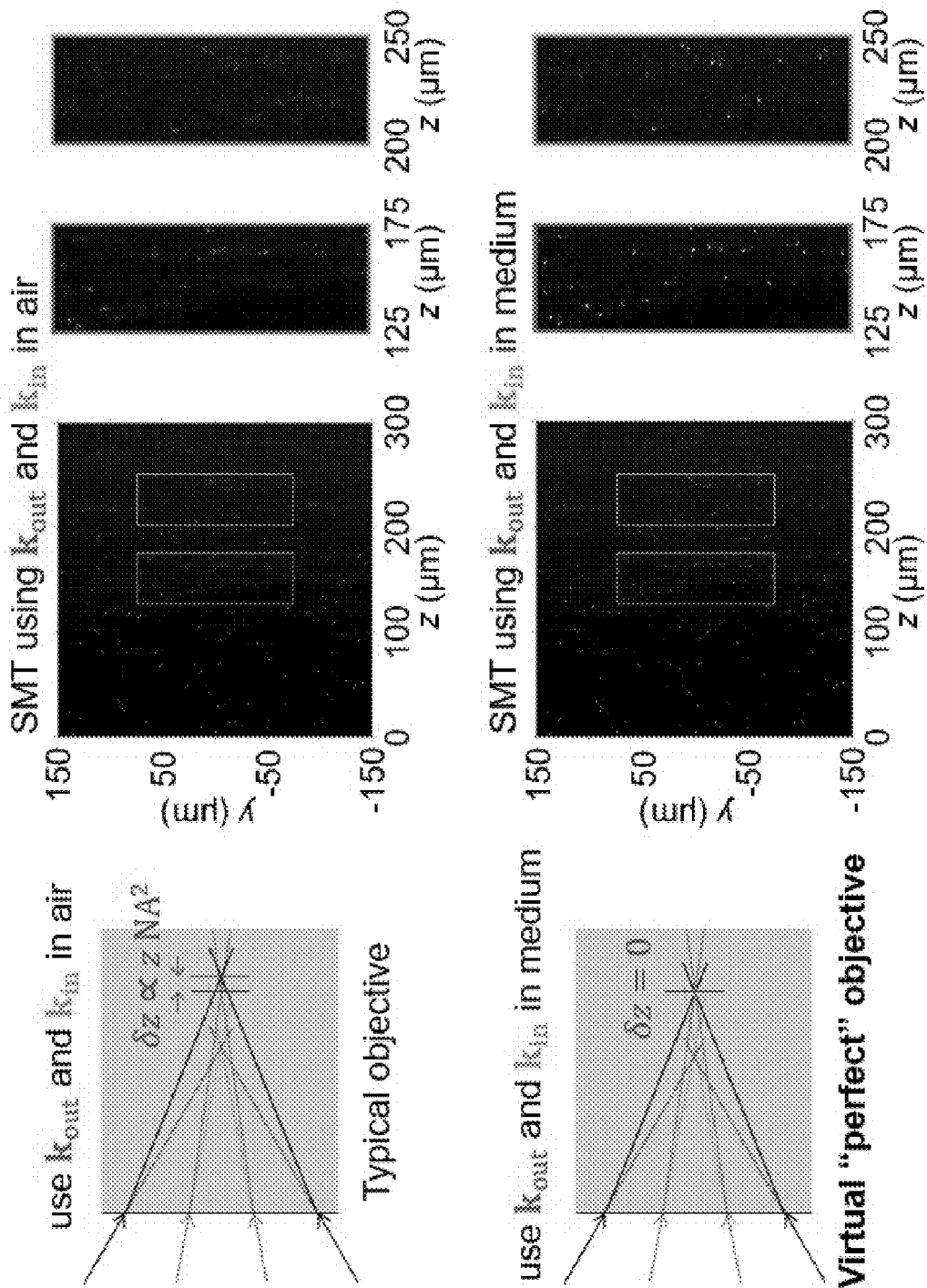
FIG. 17. Methodology for correcting for refractive index mismatch between air and the sample target.

FIG. 17 depict methodology for correcting for refractive index mismatch between air and the sample target. In this regard, the interface between air and the sample target affects focusing by a typical objective in that the focus shifts light from different angles resulting in a focus to different points which degrades the focusing quality. This can be corrected digitally in SMT by using use the momentum in the medium itself. This effectively creates the input and output wave front perfectly focused to a single point for all different angles across every depth that is scanned.

FIG. 18 provides a table comparing the SMT and other imaging methods. SMT can image deeper than the other methods maintaining high lateral and axial resolutions across a large volume by digital scanning while correcting index mismatch between a target and air. In the simulations, the tissue phantom is homogeneous in a sense that its effective index is roughly the same across the volume. However, in real biological tissue, there will be strong spatially inhomogeneities that also give rise to spatial aberration which can be digitally corrected.

Figure 19:
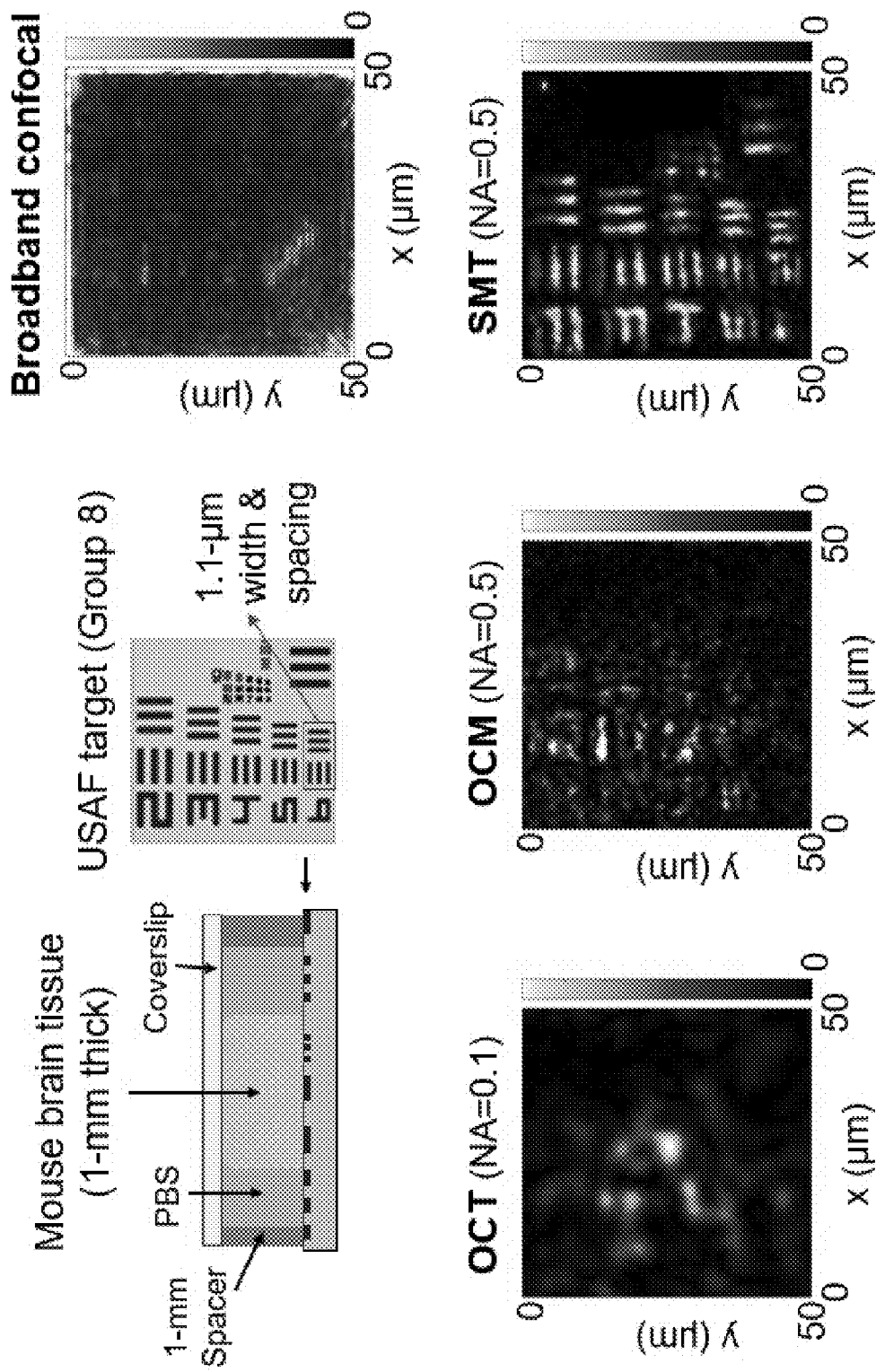
FIG. 19. Results for examining a USAF target that is buried underneath a millimeter of mouse brain tissue.

FIG. 19 provides experimental results for examining a USAF target that is buried underneath a millimeter of mouse brain tissue. FIG. 19 provides a comparison between broadband confocal, OCT, OCM, and SMT. In the broadband confocal method, the summation over frequencies is incoherent whereas in the SMT method the summation is coherent. Therefore, in the broadband confocal method time gating is ineffective in suppressing multiple scattered light resulting in no image at the depths of the USAF target. With OCT (NA=0.1), a better gating rejection of multiple scattered light is observed but with low spatial gating and low resolution. When the NA is increased to 0.5 we have OCM then we have better spatial gating now we start to some feature of the USAF target but we still cannot see the structure. The SMT results show a significant improvement in the image clarity. The SMT images have been corrected for spatial and chromatic aberration of the optical system by calibrating against a mirror. Sample's dispersion was corrected for by optimizing the spectral phase. The SMT images have also corrected for index mismatch correction as described above. Finally, optimization over the angle-dependent phase corrects for spatial aberration of mouse brain tissue.

Figure 20:
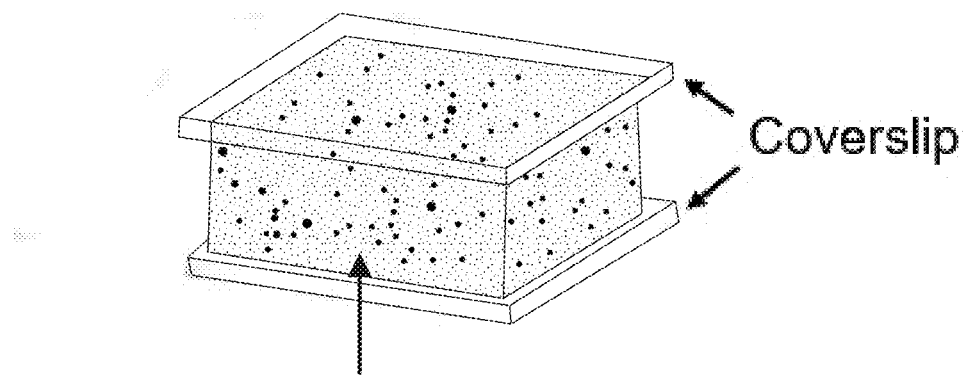
FIG. 20. Schematic for the arrangement of a sample for 3D imaging.
Figure 21A:
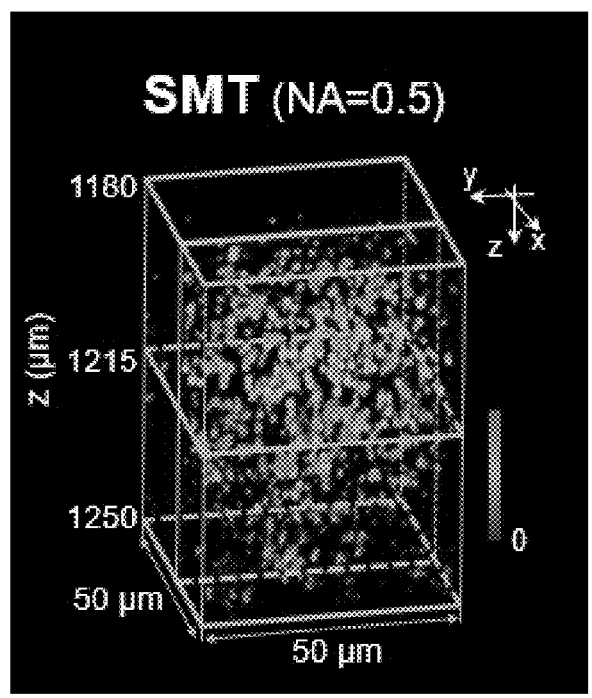
FIGS. 21A, 21B, 21C, 21D, 21E, 21F, 21G, and 21H. 3D image of the $TiO_2$ nanoparticles for various imaging technologies.
Figure 21B:
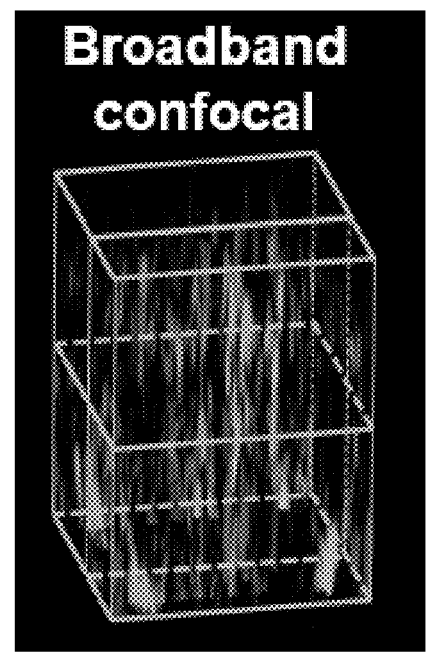
Figure 21C:
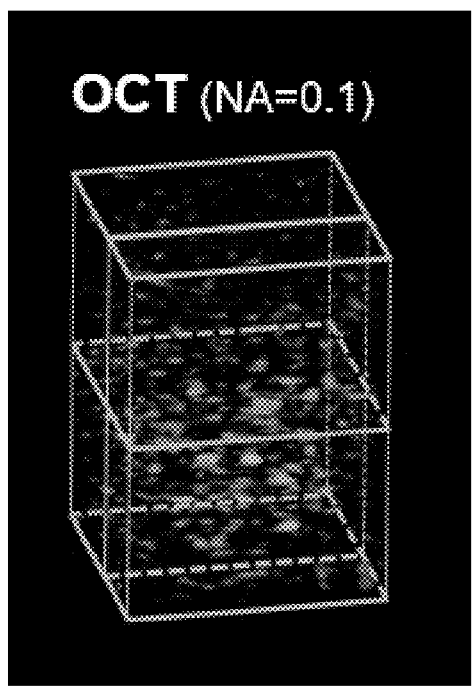
Figure 21D:
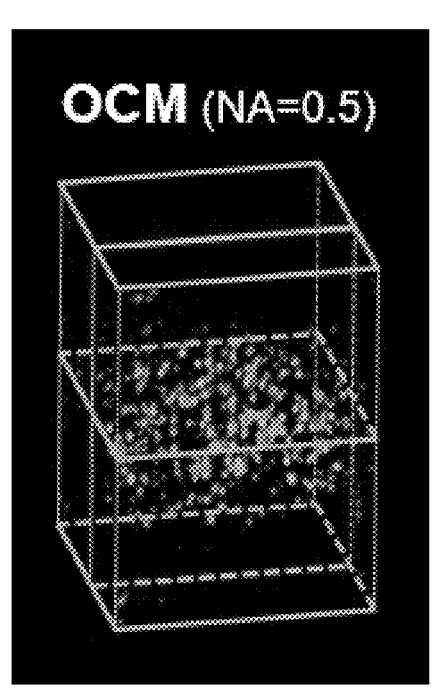
Figure 21E:
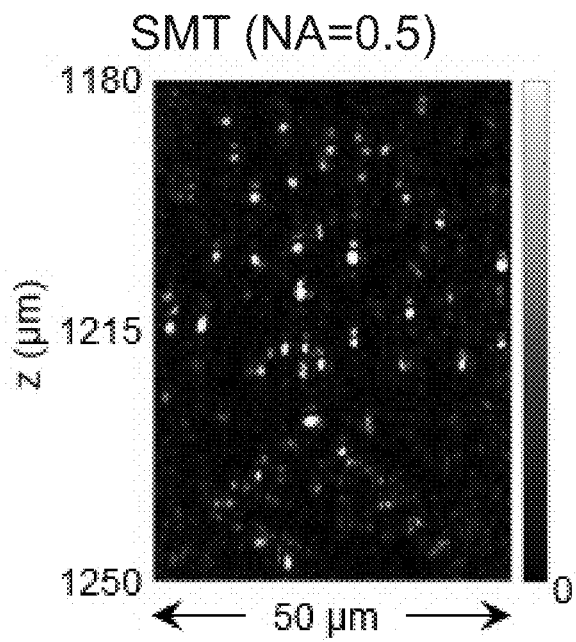
Figure 21F:
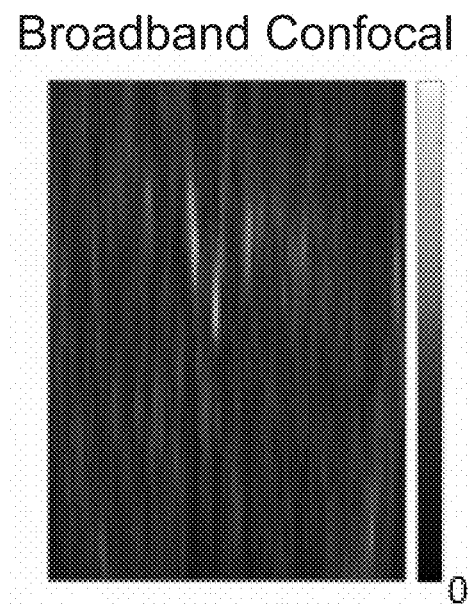
Figure 21G:
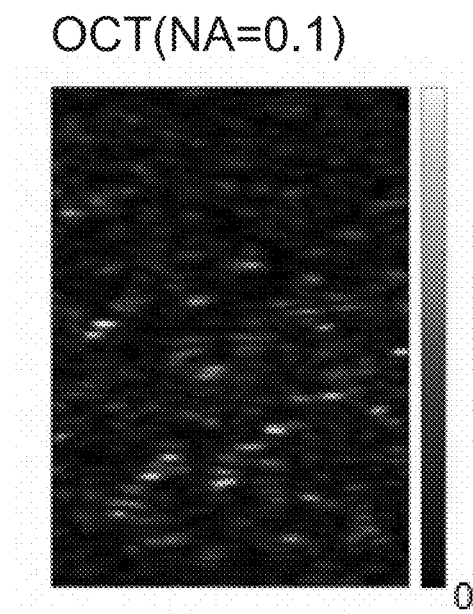
Figure 21H:
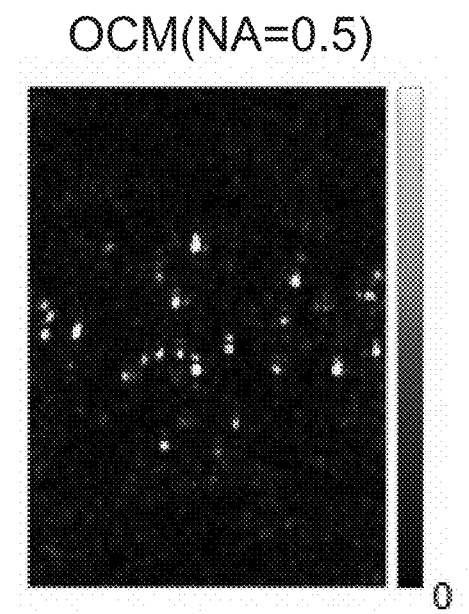

FIGS. 20, 21A, 21B, 21C, 21D, 21E, 21F, and 21G demonstrate the applicability of SMT to 3D imaging. FIG. 20 provides a schematic for the arrangement of a sample for 3D imaging. FIG. 21 provide 3D image of the $TiO_2$ nanoparticles for various imaging technologies. SMT provides clear images while broad band confocal shows poor resolution with barely any features being observed. OCT provides low lateral resolution while OCM only shows nanoparticles near the focal plane.

Figure 22:
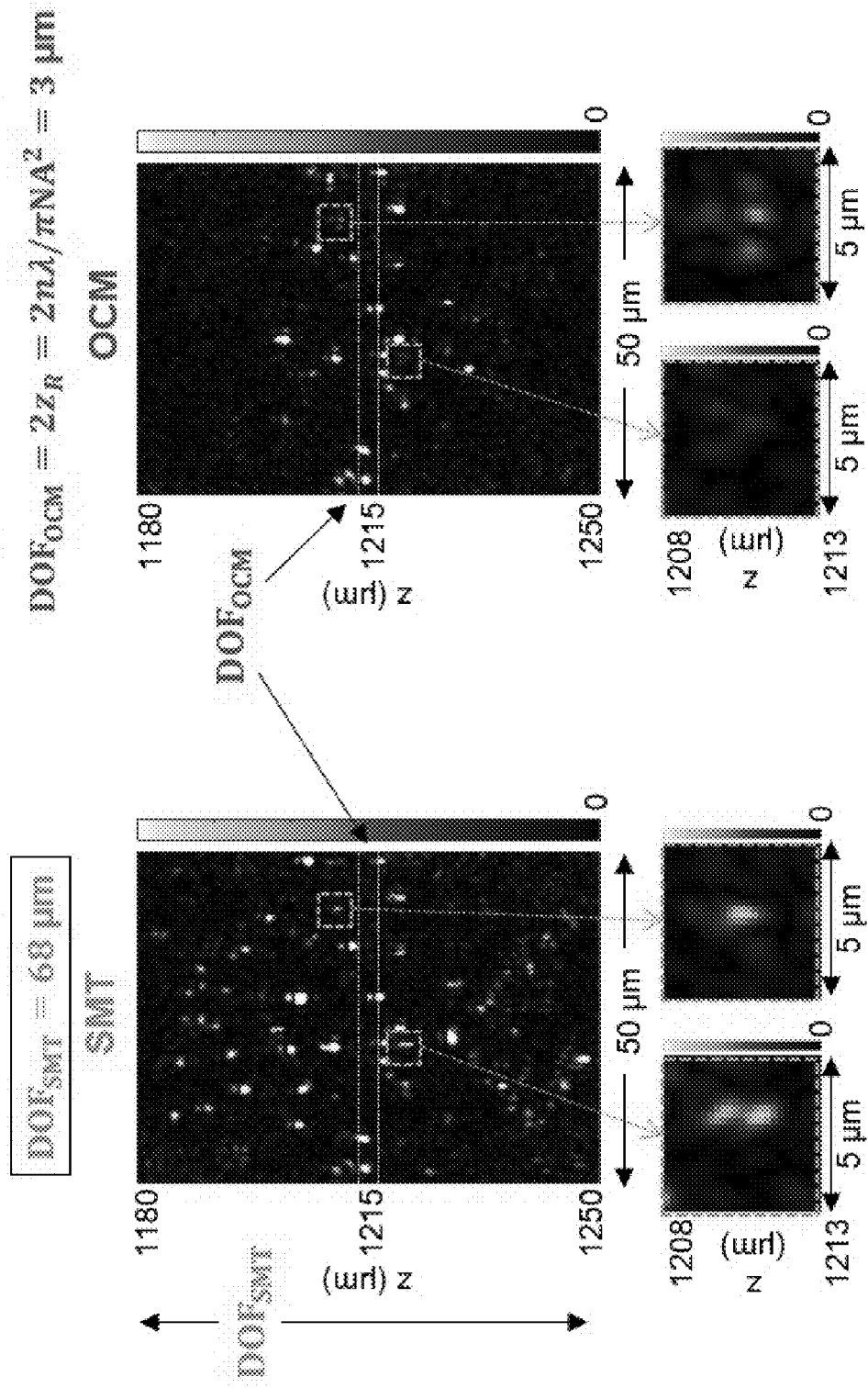
FIG. 22. Depth of field comparison between SMT and OCM.
Figure 23:
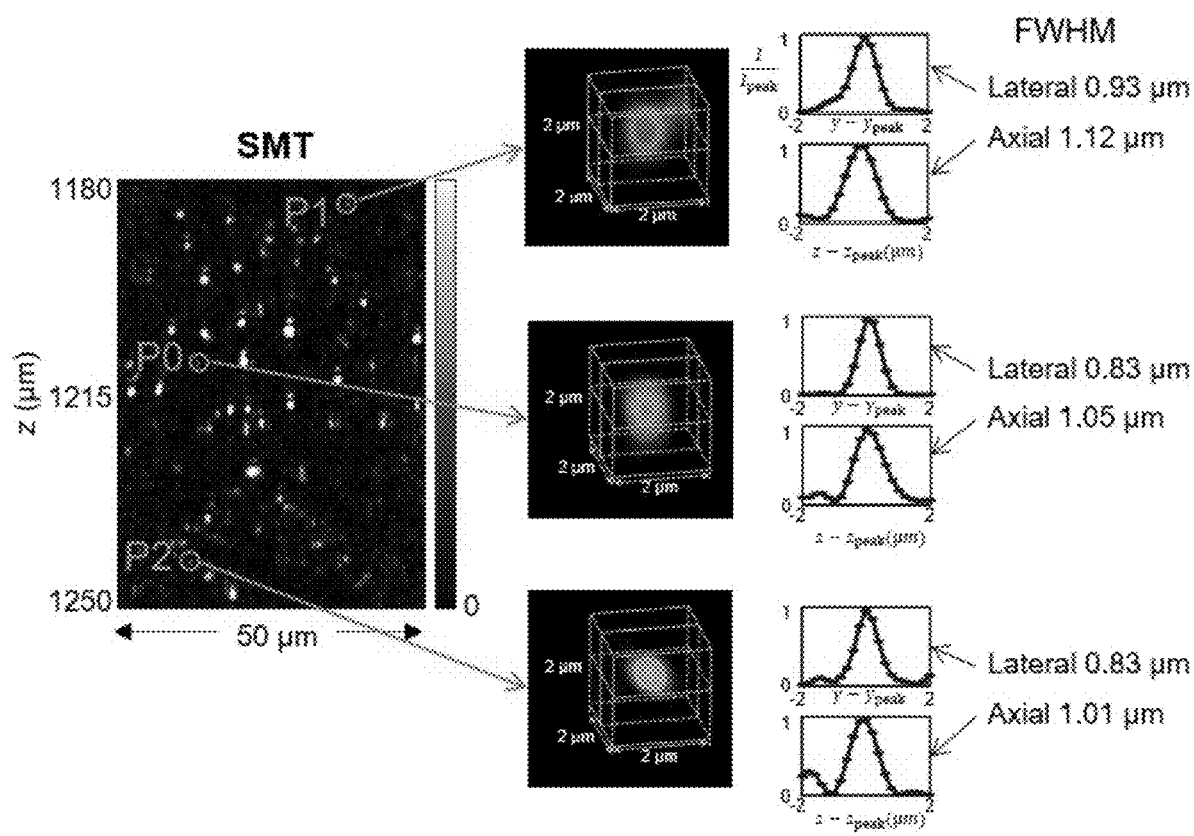
FIG. 23. Resolution of SMT.

FIG. 22 provides a depth of field (DOF) comparison between SMT and OCM. The depth of field is defined as when the lateral resolution degrades by a factor of V. For OCM, the DOF is twice the Rayleigh length. In contrast to SMT, OCM does not have good spatial focus outside of its depth of field. FIG. 23 provides plots for axial and lateral resolution at different sample locations.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for multi-spectral scattering-matrix tomography comprising
   a) splitting an input light signal into an incident light signal and a reference light signal, wherein the input light signal is varied over a predetermined frequency range;
   b) directing the incident light signal to a sample in either a reflection configuration or a transmission configuration such that an output light signal includes light scattered from or transmitted through the sample, wherein the incident light signal is varied over a predetermined range of incident angles;
   c) directing the output light signal and the reference light signal to a camera, the output light signal directed at a constant angle with respect to the reference light signal to allow for amplitude and phase to be calculated by off-axis holography;
   d) measuring with the camera a total light signal that is a coherent sum of the reference light signal and the output light signal;
   e) collecting the total light signal for each light frequency and each incident angle as collected total light signal data;
   f) calculating with a computing device a scattering matrix or a reflection matrix or a transmission matrix from the collected total light signal data; and
   g) deriving an image of the sample from the scattering matrix or reflection matrix or transmission matrix by summing over angles and summing over light frequencies, wherein an image intensity is determined from the scattering matrix by:

$$I_{SMT}(r_0) = \left| \sum_\omega \sum_{k_{out}} \sum_{k_{in}} e^{i(k_{out}-k_{in})\cdot r_0} S(\omega, k_{out}, k_{in}) \right|^2$$

where:
$I_{SMT}$ is the image intensity as a function of position $r_0$ in the sample;
$r_0$ is a position vector of a point in the sample;
$S(\omega, k_{out}, k_{in})$ is an element of the scattering matrix for the incidence channel with $k_{in}$ and the reflection channel with $k_{out}$;
$k_{in}$ is the wavevector of the incident light signal;
$k_{out}$ is the wavevector of the output (i.e., reflected) light signal; and
$\omega$ is the light frequency.

2. The method of claim 1, wherein the scattering matrix, the reflection matrix or the transmission matrix is determined by Fourier transforming the collected total light signal data to form a transformed collected total signal data and performing an inverse Fourier transform on a first-order region of the transformed collected total signal data to determine amplitude and phase of the output light signal.

3. The method of claim 1 wherein an image intensity is determined from the reflection matrix by:

$$I_{SMT}(r_0) = \left| \sum_\omega \sum_{k_{out}} \sum_{k_{in}} e^{i(k_{out}-k_{in})\cdot r_0} R(\omega, k_{out}, k_{in}) \right|^2$$

where:
$I_{SMT}$ is the image intensity as a function of position $r_0$ in the sample;
$r_0$ is a position vector of a point in the sample;
$R(\omega, k_{out}, k_{in})$ is an element of the reflection matrix for the incidence channel with $k_{in}$ and the reflection channel with $k_{out}$;
$k_{in}$ is the wavevector of the incident light signal;
$k_{out}$ is the wavevector of the output (i.e., reflected) light signal; and
$\omega$ is the light frequency.

4. The method of claim 1 wherein an image intensity is determined from the reflection matrix by:

$$I(r) \propto \left| \int d\omega \sum_{b,a} e^{i k_b \cdot r} r_{ba} e^{-i k_a \cdot r} \right|^2$$

where:
I(r) is the image intensity as a function of position r in the sample;
r is a position vector of a point in the sample;
$r_{ba}$ is an element of the reflection matrix for an a-th incidence and b-th reflection channel;
a is a label for a channel of incidence;
b is a label for a channel of reflection;
$k_a$ is the wavevector of the incident light signal;
$k_b$ is the wavevector of the output light signal; and
ω is the light frequency.

5. The method of claim 4 wherein the image intensity is expressible as:

$$I(r) \propto |\int d\omega (A\_r\hat{}\text{Born})\hat{}\dagger r')|\hat{}2.$$

6. The method of claim 1 wherein an image intensity is determined from the transmission matrix by:

$$I(r) \propto \left| \int d\omega \sum_{b,a} e^{ik_b \cdot r} t_{ba} e^{-ik_a \cdot r} \right|^2$$

where:
I(r) is the image intensity as a function of position r in the sample;
r is a position vector of a point in the sample;
$t_{ba}$ is an element of the transmission matrix for an a-th incidence and b-th transmitted channel;
a is a label for an angle of incidence;
b is a label for an angle of transmitted light;
$k_a$ is the wavevector of the incident light signal;
$k_b$ is the wavevector of the output light signal; and
ω is the light frequency.

7. The method of claim 1 further comprising modifying input light signal intensity over the predetermined frequency range to minimize light intensity differences.

8. The method of claim 7, wherein the input light signal intensity is modified with a light attenuator.

9. The method of claim 1, wherein the incident light signal is varied over the predetermined range of incident angles with a galvanometer scanner.

10. The method of claim 9, wherein the galvanometer scanner and the camera are synchronized with a trigger signal.

11. The method of claim 1, wherein the reference light signal is spatially filtered to provide a cleaner and Gaussian-like beam profile.

12. A multi-spectral scattering-matrix tomography system comprising:
a tunable laser providing an input light signal having a light frequency varied over a predetermined frequency range;
a beam splitter configured to split the input light signal into an incident light signal and a reference light signal;
a galvanometer scanner configured to direct the incident light signal to a sample, wherein the incident light signal is varied over a predetermined range of incident angles;
a first set of optical components configured to direct the incident light signal to the sample in either a reflection configuration or a transmission configuration such that an output light signal includes light scattered from or transmitted through the sample;
a camera configured to measure a total light signal that is a coherent sum of the reference light signal and the output light signal;
a second set of optical components configured to direct the output light signal and the reference light signal to the camera, the output light signal being directed at a constant angle with respect to the reference light signal to allow for amplitude and phase to be calculated by off-axis holography;
a computing device in electrical communication with the camera, the computing device configured to collect the total light signal for each light frequency and each incident angle as collected total light signal data, to calculate a scattering matrix or a reflection matrix or a transmission matrix from the collected total light signal data; and to derive an image of the sample from the reflection matrix or transmission matrix by summing over angles and summing over light frequencies;
wherein the computing device is further configured to determine the scattering matrix or the reflection matrix or the transmission matrix by Fourier transforming the collected total light signal data to form a transformed collected total signal data and performing an inverse Fourier transform on a first-order region of the transformed collected total signal data to determine amplitude and phase of the output light signal and wherein the computing device is further configured to determine an image intensity from the reflection matrix by:

$$I(r) \propto \left| \int d\omega \sum_{b,a} e^{ik_b \cdot r} r_{ba} e^{-ik_a \cdot r} \right|^2$$

where:
I(r) is the image intensity as a function of position r in the sample;
r is a position vector of a point in the sample;
$r_{ba}$ is an element of the reflection matrix for an a-th incidence and b-th reflection channel;
a is a label for an angle of incidence;
b is a label for an angle of reflection;
$k_a$ is the wavevector of the incident light signal;
$k_b$ is the wavevector of the output light signal; and
ω is the light frequency.

13. The system of claim 12, wherein the computing device is further configured to determine an image intensity from the transmission matrix by:

$$I(r) \propto \left| \int d\omega \sum_{b,a} e^{ik_b \cdot r} t_{ba} e^{-ik_a \cdot r} \right|^2$$

where:
I(r) is an image intensity as a function of position r in the sample;
r is a position vector of a point in the sample;
$t_{ba}$ is an element of the transmission matrix for an a-th incidence and b-th transmitted channel;
a is a label for an angle of incidence;
b is a label for an angle of transmitted light;
$k_a$ is the wavevector of the incident light signal;
$k_b$ is the wavevector of the output light signal; and
ω is the light frequency.

14. The system of claim 12, further comprising a light attenuator configured to modify input light signal intensity over the predetermined frequency range to minimize light intensity differences.

15. The system of claim 12, wherein the galvanometer scanner and the camera are synchronized with a trigger signal.

16. The system of claim 12, further comprising a spatial filter configured to spatially filter the reference light signal to provide a cleaner and Gaussian-like beam profile.

* * * * *